US005837499A

United States Patent [19]

[11] Patent Number: 5,837,499

[45] Date of Patent: Nov. 17, 1998 van Oostrum et al.

[54] DNA ENCODING C5A RECEPTOR ANTAGONISTS HAVING SUBSTANTIALLY NO AGONIST ACTIVITY AND METHODS OF EXPRESSING SAME

[75] Inventors: Jan van Oostrum, Flueh, Switzerland; William C. Boyar, New Providence; Nicholas G. Galakatos, Summit, both of N.J.; Albert Schmitz, Basel; Gino Van Heeke, Witterswil, both of Switzerland

[73] Assignee: Ciba-Geigy Corporation, Tarrytown, N.Y.

[21] Appl. No.: 463,377

[22] Filed: Jun. 5, 1995

Related U.S. Application Data

[63] Continuation-in-part of PCT/IB94/00359 Nov. 16, 1994, which is a continuation-in-part of Ser. No. 162,591, Dec. 6, 1993, abandoned.

[51] Int. Cl.[6] .......................... C12P 21/00; C07K 14/435; C12N 15/12

[52] U.S. Cl. ........................ 435/69.6; 435/69.7; 435/70.1; 435/71.1; 435/320.1; 435/252.3; 435/254.11; 435/325; 435/252.33; 530/408; 536/23.4; 536/23.5

[58] Field of Search ................................. 435/69.6, 69.7, 435/70.1, 71.1; 530/408; 536/23.4, 23.5

[56] References Cited

U.S. PATENT DOCUMENTS

| | | | |
|---|---|---|---|
| 4,620,948 | 11/1986 | Builder et al. | 530/419 |
| 4,686,100 | 8/1987 | Raffin et al. | 424/158.1 |
| 4,692,511 | 9/1987 | Hahn | 530/325 |
| 4,772,584 | 9/1988 | Cleary | 514/2 |
| 4,937,189 | 6/1990 | Davidow et al. | 435/6 |
| 5,177,190 | 1/1993 | Rollins et al. | 530/350 |
| 5,190,922 | 3/1993 | Luly et al. | 514/18 |
| 5,614,370 | 3/1997 | Konteatis et al. | 435/7.21 |

FOREIGN PATENT DOCUMENTS

| | | |
|---|---|---|
| 0245993 | 11/1987 | European Pat. Off. . |
| 9009162 | 8/1990 | WIPO . |
| 9210205 | 6/1992 | WIPO . |
| 9211858 | 7/1992 | WIPO . |
| 95/16033 | 6/1995 | WIPO . |

OTHER PUBLICATIONS

Marston et al. Solubilization of Protein Assiegates. Methods in Enzymology. vol. 182, pp. 264–277. 1990.

Franke et al. Human C5A Anaplylatoxin: Gene Synthesis, Expression, and Recovery of Biologically Active Material From *Escherichia coli.* Methods in Enzymology vol. 162, pp. 653–668. 1988.

Canova–Davis et al. Chemical Heterogeneity as a Result of Hydroxylamine Cleavage of a Fusion Protein of Human Insulin–Like Growth Factor I. Biochemical Journal. vol. 285, pp. 207–213. 1992.

Kinoshita, Immunology Today 12:291–300 (1991).

Muller–Eberhard, Ann. Rev. Biochem 57:321–347 (1988).

Nilsson et al., J. Immunol. 114:815–822 (1975).

Hugli, CRC Crit. Rev. Immunol. 1:321–366 (1981).

Bautsch et al., Immunobiol. 185:41–52 (1992).

Fernandez, et al., J. Immunol. 120:109–115 (1978).

Bautsch et al., Biochem J. 288:261–266 (1992).

Haslett et al., J. Immunol. 142:3510–3517 (1989).

Mollison et al., Proc. Nat'l. Acad. Sci. USA 86:292–296 (1989).

Hammerschmidt, et al., Lancet 1:947–49 (1980).

Kawai et al., J. Med. Chem. 35:220–223 (1992).

Kawai et al., J. Med. Chem. 34:2068–2071 (1991).

Or et al., J. Med. Chem. 35:402–406 (1992).

Mollison et al., "C5a Structural Requirements for Neutryphil Receptor Interaction," in Progress in Inflammation Research and Therapy, Birkhaus Verlag, Basel (1991), pp. 17–21.

Oppermann et al., J. Immunol. 151(7):3785–3794 (1993).

Chenoweth et al., Mol. Immunol. 17:151–161 (1980).

Seligmann et al., Agents and Actions 21:375–378 (1987).

Fernandez et al., J. Biol. Chem. 253:6955–6964 (1978).

Mandecki et al., PROC. Nat'l. Acad. Sci. USA 82:3543–3547 (1985).

Carney et al., Protein Science 2:1391–1399 (1993).

Goff et al., Proc. Nat'l. Acad. Sci. USA 81:6647–6651 (1984).

Harris et al., J. Receptor Res. 11:115–128 (1991).

Rollins et al., J. Biol. Chem. 263:520–526 (1988).

Braunwalder et al., Mol. Immunol. 29(11):1319–1324 (1992).

Hensens et al., J. Antibiotics 44(2):249–254 (1991).

Greer et al., "Comparative Modeling of Proteins in the Complement Pathway"in *Computer–Assisted Modeling of Receptor–Ligand Interactions: Theoretical Aspects and Applications to Drug Design:* pp. 385–397 (1989).

Ayesh et al., J. Immunol. 144(8):3066–70 (1990).

Ember et al., J. Immunol. 148(10):3165–73 (1992).

Chenoweth et al., Proc. Natl. Acad. Sci. USA 75:3943–3947 (1978).

Gerard et al., Annu. Rev. Immunol. 12:775–808 (1994).

*Primary Examiner*—Stephen Walsh
*Assistant Examiner*—Brian Lathrop
*Attorney, Agent, or Firm*—Lerner, David, Littenberg, Krumholz & Mentlik

[57] ABSTRACT

Disclosed are polypeptide analogues of human C5a which are C5a receptor antagonists that exhibit substantially no analphylatoxin or agonist activity, and derivatives of the analogues, and dimeric forms of the analogues or derivatives. DNA molecules encoding the polypeptides and methods of making the analogues are also provided. Pharmaceutical formulations containing a C5a analogue, are used therapeutically in the treatment of C5a-mediated diseases and inflammatory conditions in mammals, and prophylactically to prevent or reduce inflammation caused by an event which causes inflammation or aggravates an existing inflammatory condition, respectively. Further disclosed are antibodies specific to the C5a analogues, derivatives thereof, and dimers of the analogues and derivatives which exhibit substantially no cross-reactivity with human C5a. The antibodies are used to detect or quantify circulating C5a analogue or derivative, as well as to modify, e.g., neutralize, the activity of the C5a receptor antagonist in vivo.

45 Claims, 2 Drawing Sheets

DNA ENCODING C5A RECEPTOR ANTAGONISTS HAVING SUBSTANTIALLY NO AGONIST ACTIVITY AND METHODS OF EXPRESSING SAME

CROSS-REFERENCE TO RELATED APPLICATIONS

This application is a continuation-in-part application of PCT-IB94-00359, filed Nov. 16, 1994, which is a continuation-in-part of U.S. patent application Ser. No. 08/162,591, filed Dec. 6, 1993, now abandoned, the contents of which are hereby incorporated by reference in their entirety.

FIELD OF THE INVENTION

The present invention relates to the field of immunology, and more specifically to the treatment: of complement-mediated diseases and inflammatory conditions in mammals.

BACKGROUND OF THE INVENTION

Inflammation is a localized, protective event, elicited by injury, which serves to destroy, dilute or wall off both injurious agents and the injured tissues. It involves a complex series of events, including dilation of arteries, capillaries and venules, with increased vascular permeability, increased blood flow, and exudation of fluids and plasma proteins. These processes are often rapidly followed by adhesion of leukocytes to the vascular endothelium, with subsequent influx of the cells into the surrounding tissue.

The complement system, a major immunological defense mechanism against foreign substances, has been shown to influence each of the factors that comprise the inflammatory response. In general, complement comprises a set of proteins that work to eliminate microorganisms, and other antigens from tissues and blood. This task is achieved either by complement components alone or in cooperation with antibodies or with cells that express complement receptors. More specifically, the system consists of about 30 plasma proteins, their corresponding cellular receptors and several membrane regulatory proteins. Kinoshita, Immunology , 12:291–300 (1991). Activation of the complement system by, for example, antigen-antibody complexes or bacterial surface structures, triggers an amplification cascade of proteolytic cleavage and protein assembly events of the complement components, which ultimately leads to the destruction and final elimination of the foreign body. Muller-Eberhard, Annu. Rev. Biochem. 57:321–347 (1988).

Several biologically active peptides are generated by the activation of the complement system. C5a, a glycoprotein containing 74 amino acids and having an $M_r$ of about 11,000, is generated by the proteolytic cleavage of the N-terminal end of C5, the fifth component of complement, by C5 convertase. Nilsson et al., J. Immunol. 114:815–822 (1975). The biological properties of C5a extend across a multitude of cells and tissues involved in both acute and chronic inflammatory processes. Hugli, CRC Crit. Rev. Immunol. 1:321–366 (1981). Mary of these properties are immunologically beneficial. C5a has been found to mediate host defense mechanisms in response to various pathological conditions. C5a participates in a wide variety of specific biologic functions commonly associated with the inflammatory response, such as smooth muscle contraction, an increase in vascular permeability, wheal and flare generation when injected into human skin, histamine release from mast cells, and induction of the oxidative burst and lysosomal enzyme release from polymorphonuclear leukocytes (PMNLs). C5a stimulates measurable responses from every circulating white blood cell including basophils, eosinophils, monocytes, and neutrophils. Hugli, supra.; Bautsch et al., Immunobiol. 185:41–52 (1992). C5a has further been found to be a potent chemoattractant. Fernandez et al., J. Immunol. 120:109–115 (1978). This protein is a pivotal stimulus to the attraction of PMNLs such as phagocytic cells to the site of inflammation.

Complement is beneficial when directed against an appropriate target such as invading microorganisms or tumor cells, but has clear pathogenic potential if activated inappropriately. For instance, the anaphylatoxins, e.g., C5a, have been implicated as causative or aggravating factors in the pathogenesis of several inflammatory diseases such as adult respiratory distress syndrome and rheumatoid arthritis. Bautsch et al., Biochem. J. 288:261–266 (1992); Haslett et al., J. Immunol. 142:3510–3517 (1989). In particular, the aberrant presence of C5a in tissue has been detected in patients afflicted with rheumatoid arthritis, osteoarthritis, psoriasis and noncardiac pulmonary edema. C5a has been found to be a principal inflammatory mediator produced by complement activation by virtue of additional activities that include recruitment and stimulation of inflammatory leukocytes and augmentation of antibody production. See Mollison et al., Proc. Natl. Acad. Sci. USA 86:292–296 (1989).

The in vivo or pharmacologic control of inflammation is presumed to be dependent on the modulation of chemotaxis. Three levels at which inhibition can occur have been recognized. These are (1) suppression of the leukocytic response to chemotactic stimuli; (2) prevention of chemotaxin generation; and (3) inactivation of the chemotaxins. In addition, because C5a exerts its various functions by binding to a specific C5a receptor found in the membrane of several human cells such as neutrophils, eosinophils and monocyte-derived cells, the inhibition of C5a-mediated chemotaxis, and in particular, the design of C5a receptor antagonists have attracted considerable attention.

U.S. Pat. No. 4,772,584 to Cleary et al. discloses polypeptides isolated from group A streptococci which inhibit the binding of C5a to PMNLs by cleaving a six amino acid peptide from the C-terminus of C5a. U.S. Pat. No. 4,692,511 to Hahn teaches polypeptide receptor antagonists to C5a which contain an essential core tetrapeptide Tyr-Asp-Gly-Ala (SEQ ID NO. 1) or Asp-Gly-Ala-Tyr (SEQ ID NO. 2), or core tripeptide Asp-Gly-Ala which display C5a blocking activity.

U.S. Pat. No. 5,190,922, WO 90/09162 and WO 92/11858 to Abbott Laboratories disclose various oligopeptides which bind to C5a receptors and purportedly modulate anaphylatoxin activity. However, several of these molecules have been shown to retain significant agonist activity. See Mollison et al., "C5a Structural Requirements for Neutrophil Receptor Interaction," in *Progress in Inflammation Research and Therapy*, Birkhauser Verlag, Basel (1991) at pages 17–21; Kawai et al., J. Med. Chem. 35:220-223 (1992); Kawai et al., J. Med. Chem. 34:2068–2071 (1991); and Or et al., J. Med. Chem. 35:402–406 (1992). Hence, there remains a strong need for a potent and therapeutically effective C5a receptor antagonist which is substantially void of agonist activity.

SUMMARY OF THE INVENTION

One aspect of the present invention is directed to polypeptidic analogues of human C5a which are C5a receptor antagonists and exhibit substantially no anaphylatoxin or agonist activity, derivatives of the analogues, and dimeric forms of the analogues and derivatives. DNA molecules encoding the polypeptides, (i.e., the analogues and derivatives thereof) plasmids, vectors and host cells transformed with the DNA molecules, and methods of preparing the C5a analogues are also provided.

Pharmaceutical formulations containing a C5a analogue, derivative or dimer thereof are advantageously used in methods for the treatment of C5a-mediated inflammatory conditions and diseases in mammals, and as a prophylactic to prevent such inflammation.

Another aspect of the present invention is directed to antibodies specific to the C5a analogue and derivatives thereof, which exhibit substantially no cross-reactivity with human C5a. The antibodies are used to detect or quantify circulating C5a analogues and derivatives in subjects (previously administered with same) as well as to modify, e.g., neutralize, the activity of the C5a analogues and derivatives in vivo.

BRIEF DESCRIPTION OF THE FIGURES

FIG. 2 is a plasmid map of pB-6/C5a.

DESCRIPTION OF THE PREFERRED EMBODIMENTS

Figure 1:
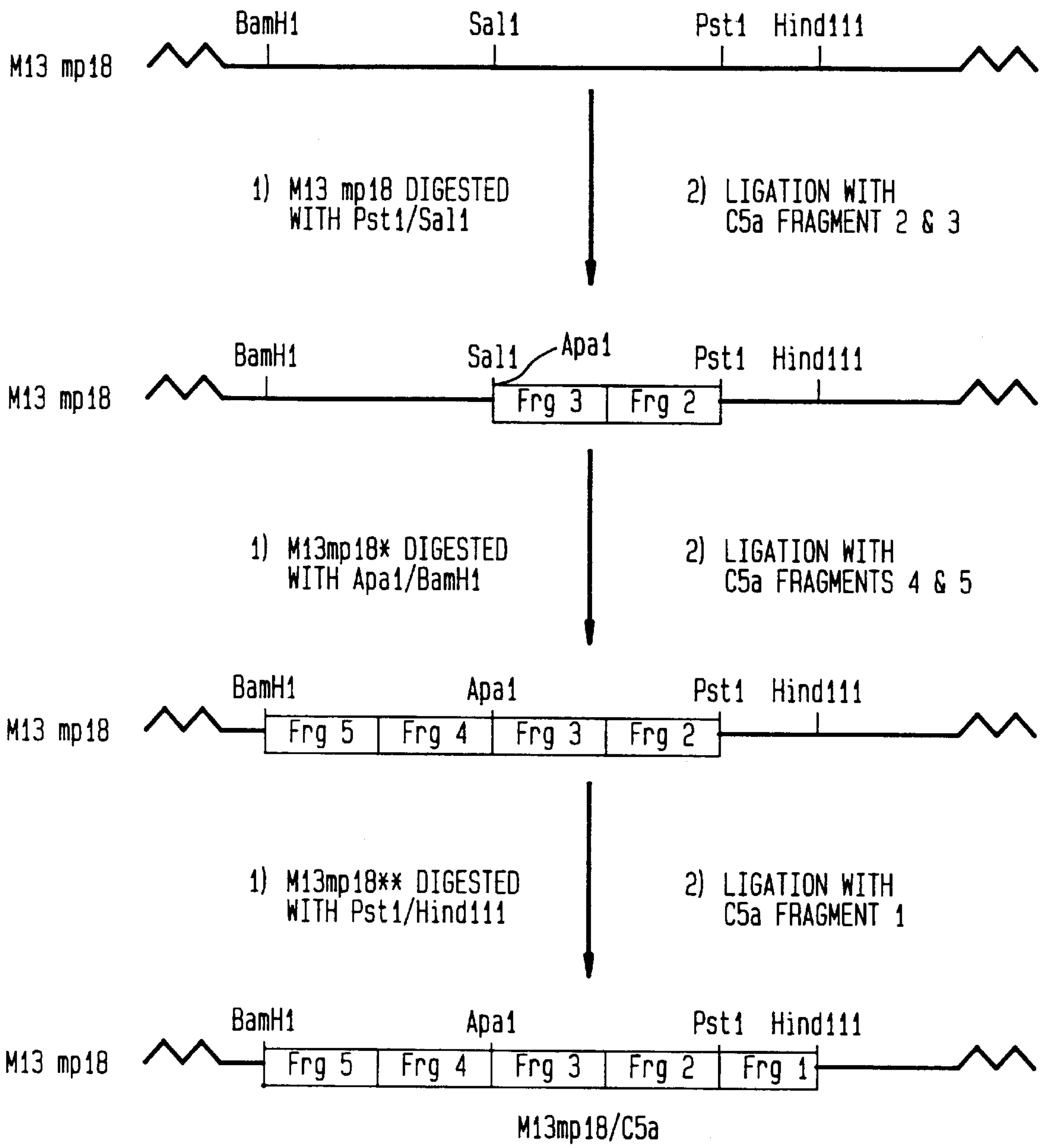
FIG. 1 is a flow diagram that illustrates the synthesis of a synthetic gene encoding human C5a via oligonucleotide coupling.

The C5a polypeptide analogues of the present invention are C5a receptor antagonists which have substantially no agonist activity. The term "C5a receptor" is understood in the art as referring to the sites on the surfaces of human blood cells such as PMNLs and monocytic cells, to which C5a, its degradation product C5a-desArg, and the instant antagonists bind. See, for example, U.S. Pat. No. 5,177,190 and Oppermann et al, J. Immunol. 151(7):3785–3794 (1993). C5a is converted enzymatically to C5a-desArg in human serum by a carboxypeptidase B-like enzyme, and is the major physiological end product in man. Chenoweth et al., Mol. Immunol. 17:151–161 (1980).

By the term "antagonist," it is meant that the instantly disclosed polypeptides are inhibitors of C5a. That is, they interfere with the binding of C5a to the C5a receptor. While not intending to be bound by any particular theory, Applicants believe that the C5a analogues are competitive inhibitors of C5a in that they compete with C5a for binding to the C5a receptor.

The antagonism of the instant C5a analogues may be quantified as an $IC_{50}$ in the calcium rise assay disclosed in Agents and Actions 21:375–378 (1987), described in detail in Example 7. The $IC_{50}$ is defined as the concentration of C5a analogue which inhibits 50% of the intracellular mobilization of calcium ions by the PMNLs bearing the C5a receptor, after a challenge dose with 100 pM human C5a. The C5a receptor antagonists of the present invention exhibit an $IC_{50}$ of no greater than about $2.0\times10^{-6}$ M in the calcium rise assay disclosed in Seligmann et al.

By the phrases "substantially no anaphylatoxin activity" or "substantially no agonist activity," it is meant that the binding of the C5a analogue (hereinafter used interchangeably with C5a receptor antagonist) to the receptor does not result in an endogenous signal transduction event ultimately resulting in the physiological responses commonly associated with anaphylatoxin-induced inflammation caused by binding of C5a to its receptor, such as activation of phagocytic cells, smooth muscle contraction, increase in vascular permeability, and excessive production of inflammatory mediators, e.g., histamines, prostaglandins, thromboxatnes, leukotrienes, interleukin (IL)-1, IL-6 and IL-8. See Hugli et al., CRC Crit. Rev. Immunol. 1:321–326 (1981) and PCT WO 92/10205. A quantitative measure of this property may also be obtained using the calcium rise assay disclosed in Seligmann et al., supra, also described in Example 7. $EC_{50}$ is a measure of agonistic activity. For purposes of the present invention, the $EC_{50}$ value is that concentration of C5a analogue which produces 50% of the maximum response caused by that same C5a analogue. Applicants have not detected agonist activity of the instant C5a analogues up to a concentration of at Least about $8.0\times10^{-7}$ M, and preferably at least about $3.0\times10^{-6}$ M in the same calcium rise assay. The C5a analogues of the present invention are those for which the $EC_{50}$ is not measurable in the Seligmann calcium rise assay up to C5a analogue concentrations of at least about $8.0\times10^{-7}$ M, and preferably at least about $3.0\times10^{-6}$ M, since no response can be detected in the assay.

C5a is a 74-amino acid polypeptide, the sequence of which has been disclosed in Fernandez et al., J. Biol. Chem. 253:6955–6964 (1978). Synthetic genes, constructed based upon the deduced nucleotide sequences, are disclosed in Mandecki et al, Proc. Nat'l Acad. Sci. USA 82:3543–3547 (1985) and U.S. Pat. No. 4,937,189 to Davidow et al. The amino acid sequence of C5a disclosed in Fernandez, and the corresponding synthetic nucleotide sequence disclosed in Davidow et al. are set forth in Table 1, below.

TABLE 1

| | | | | | | | | | | | |
|---|---|---|---|---|---|---|---|---|---|---|---|
| | | 1 | 2 | 3 | 4 | 5 | 6 | 7 | 8 | 9 | 10 |
| EcoRI | | thr (SEQ. ID. NO. 4) | leu | gln | lys | lys | ile | glu | glu | ile | ala |
| AATTCT GA | ATG TAC (SEQ. ID. NO. 3) | ACT TGA | CTG GAC | CAA GTT | AAG TTC | AAG TTC | ATC TAG | GAA CTT | GAA CTT | ATC TAG | GCT CGA |

| | | | | | | | | | | | | |
|---|---|---|---|---|---|---|---|---|---|---|---|---|
| 11 | 12 | 13 | 14 | 15 | 16 | 17 | 18 | 19 | 20 | 21 | 22 | 23 |
| ala | lys | tyr | lys | his | ser | val | val | lys | lys | cys | cys | tyr |
| GCT CGA | AAG TTC | TAC ATG | AAG TTC | CAC GTG | TCC AGG | GTC CAG | GTT CAA | AAG TTC | AAG TTC | TGT ACA | TGT ACA | TAC ATG |

TABLE 1-continued

| | | | | | | | | | | | | | |
|---|---|---|---|---|---|---|---|---|---|---|---|---|---|
| 24 | 25 | 26 | 27 | 28 | 29 | 30 | 31 | 32 | 33 | 34 | 35 | 36 | |
| asp | gly | ala | cys | val | asn | asn | asp | glu | thr | cys | glu | gln | |
| GAT | GGT | GCA | TGC | GTC | AAC | AAC | GAC | GAA | ACC | TGT | GAA | CAA | |
| CTA | CCA | CGT | ACG | CAG | TTG | TTG | CTG | CTT | TGG | ACA | CTT | GTT | |
| 37 | 38 | 39 | 40 | 41 | 42 | 43 | 44 | 45 | 46 | 47 | 48 | 49 | |
| arg | ala | ala | arg | ile | ser | leu | gly | pro | arg | cys | ile | lys | |
| CGA | GCT | GCT | CGT | ATT | TCT | CTG | GGC | CCT | CGC | TGT | ATC | AAG | |
| GCT | CGA | CGA | GCA | TAA | AGA | GAC | CCG | GGA | GCG | ACA | TAG | TTC | |
| 50 | 51 | 52 | 53 | 54 | 55 | 56 | 57 | 58 | 59 | 60 | 61 | 62 | |
| ala | phe | thr | glu | cyc | cyc | val | val | ala | ser | gln | leu | arg | |
| GCT | TTC | ACT | GAA | TGT | TGT | GTT | GTC | GCT | TCC | CAA | CTG | CGC | |
| CGA | AAG | TGA | CTT | ACA | ACA | CAA | CAG | CGA | AGG | GTT | GAC | CCG | |
| 63 | 64 | 65 | 66 | 67 | 68 | 69 | 70 | 71 | 72 | 73 | 74 | | |
| ala | asn | ile | ser | his | lys | asp | met | gln | leu | gly | arg | stop | |
| | | | | | | | | | | | | | HindIII |
| GCT | AAC | ATT | TCT | CAC | AAG | GAC | ATG | CAA | CTC | GGC | CGC | TAA | A |
| CGA | TTG | TAA | AGA | GTG | TTC | CTG | TAC | GTT | GAG | CCG | GCG | ATT | TTCGA |

Applicants have unexpectedly and surprisingly discovered that certain analogues of human C5a, produced by mutagenizing the portion of a synthetic C5a gene encoding the C-terminal region, i.e., amino acids 64–74, of human C5a (hereinafter used interchangeably with "C5a(1-74)"), have dramatically different properties than C5a. That is, they exhibit excellent antagonistic properties and substantially no agonist activity. Specifically, the C5a analogues of the present invention are defined in terms of two modifications or mutations to the C-terminal region of C5a (1-74), N'-Asn—Ile—Ser—His—Lys—Asp—Met—
(64) (65) (66) (67) (68) (69) (70)

Gln—Leu—Gly—Arg—C' (SEQ ID NO. 5),
(71) (72) (73) (74)

(amino acids 64–74 of C5a (1-74)). First, it is truncated at least to Leu (72); i.e., by removing the Gly (73) and Arg (74) residues. Second, at least one cysteine is substituted in the region, provided that the C-terminal amino acid of the polypeptide (i.e., the C-terminus) is cysteine, and that the thiol (SH) group of the C-terminal cysteine is in reduced form (i.e., has a free thiol group), or is in a form capable of spontaneously converting or being readily converted into a free thiol group.

In a preferred embodiment, from 2 to 6 of the most C-terminal amino acids are truncated from C5a (1-74). Thus, in the case where the N-terminal 63 amino acid region is kept intact and only one cysteine is substituted, the respective corresponding embodiments may be designated as follows: C5a (1-72, Leu72Cys), C5a. (1-71, Gln71Cys), C5a (1-70, Met70Cys), C5a (1-69, Asp69Cys) and C5a (1-68, Lys68Cys). In a more preferred embodiment, the C-terminal region is truncated to and including Met70, Gln71or Leu72, which correspond to the three former designated embodiments. An even more preferred embodiment is C5a (1-71, Gln71Cys).

The C-terminal region can be further truncated N-terminally to Asn 64, which would correspond to the representative designated embodiments C5a (1-67, His67Cys), C5a (1-66, Ser66Cys), C5a (1-65, Ile65Cys) and 65a (1-64, Asn64Cys), provided that the resultant C5a analogue exhibits the forementioned requisite antagonist property (an $IC_{50}$ of no greater than about $2.0 \times 10^{-6}$ M) and substantially no anaphylatoxin or agonist activity (a non-measurable $EC_{50}$ up to C5a analogue concentrations of at least $3.0 \times 10^{-6}$ M). Those skilled in the art would understand that "analogues" of human C5a do not include antibodies specific to C5a or to sites on the C5a receptor.

Derivatives of the human C5a analogues as described herein are included within the scope of the present invention. These include modifications such as point mutations, substitutions, additions and deletions in the N-terminal 63 amino acid region (amino acids 1–63 of C5a(1-74)), Carney et al., Protein Science 2:1391–1399 (1993), and further amino acid substitutions in the thus-mutagenized C-terminal region. The type and extent of the modifications are generally not important, so long as the resultant derivative remains a C5a receptor antagonist with substantially no agonist activity, both as defined above. For example, the Cys27 residue in the N-terminal region of C5a (1-74) can be changed, e.g., to a serine residue, in order to minimize complications during refolding. Thus, in a more preferred embodiment, the C5a analogue derivative is designated C5a(1-71, Cys27Ser, Gln71 Cys). Also, the N-terminus may be changed to a Methionine residue, either by substitution or addition, to allow for expression of a C5a analogue-encoding gene in various host cells such as *E. coli*. Any C5a analogue of the present invention produced in *E. coli* will have a Met residue as its N-terminus, as explained in Example 1 and shown in Table 3 (Example 3, below).

N-terminal substitutions also occur in cases where the human C5a analogs are expressed in various host cells, e.g., *E. coli*, as a fusion protein, and then isolated by cleaving the fusion protein at a convenient site. For example, cleavage of a human C5a analogue from its fusion protein partner linked via an hydroxylamine sensitive linkage, results in the substitution of a glycine (Gly) residue for the native human C5a threonine (Thr) N-terminus. Thus, in another more preferred embodiment, the C5a analogue derivative is designated C5a (1-71, Thr1Gly, Cys27Ser, Gln71Cys).

An example of a further modification of the C-terminal region is the substitution of a phenylalaniine residue for the native histidine at position 67 of C5a(1-74). Thus, in a most preferred embodiment, the C5a analogue derivative is designated C5a (1-71, Thr1Met, Cys27Ser, His67Phe, Gln71Cys).

The C5a analogues (hereinafter referring collectively to the analogues and derivatives thereof) of the present invention can be prepared via numerous procedures standard in the art. For instance, they may be prepared via direct chemical synthesis. They may also be prepared by expression of DNA molecules, i.e., synthetic genes, encoding the polypeptides in suitable host cells. These DNA molecules, deducible from the amino acid sequences of the C5a analogues, in turn may be prepared via known techniques. The DNAs may be synthesized chemically as disclosed in Narang, Tetrahedron 393:3–22(1983); EPA 146,785; Mandecki et al., Proc. Natl. Acad. Sci. USA 82:3543–3547; and (1985) (disclosing the chemical synthesis of a gene encoding C5a). Fragments of the DNA molecules may be prepared chemically, which then are linked together enzymatically. See Volume 1, Chapter 8 of *Current Protocols in Molecular Biology*, Ausubel et al. (Eds.), Wiley, N.Y. (1990).

DNAs encoding the C5a analogues of the present invention can also be prepared by mutagenesis of known synthetic or natural genes encoding C5a, such as those disclosed in Fernandez, Mandecki Davidson, for example. See Ausubel et al., supra.; Volume II, Chapter 15 of Maniatis et al., *Molecular Cloning, A Laboratory Manual*, Cold Spring Harbor, N.Y. (1989); and Mollison et al., Proc. Natl. Acad. Sci. USA 86:292–296 (1989). Further, the DNAs may be prepared via PCR techniques. *PCR Protocols*, Innis et al. (Eds.), Academic Press, San Diego, Calif. (1990).

The DNA molecules encoding the C5a analogues of the present invention are operably linked to known regulatory sequences, e.g., promoter, enhancer, 3'-untranslated sequences, and 5' translated sequences, e.g., signal and leader sequences, and then transformed into host cells capable of expressing the genes, in accordance with standard techniques. Then, the transformed host cells are cultured under conditions suitable for expression of the antagonist encoding gene. Representative host cells include prokaryotes such as *E. coli* and Bacillus, e.g., *B. subtilis*; and eukaryotes such as filmentous fungi, e.g., *Aspergillus niger*; yeast, e.g., *Saccharomyces cerevisiae, Pichia pastoris* and *Yarrowia lipolytica*; baculovirus/insect cell cultures (Summers et al., *A Manual of Methods for Baculoivirus Vectors and Insect Cell Culture Procedures*, Texas Agricultural Experiment Station (1987)); mammalian cell lines; and plants (J. Vandekerckhove et al., BIO/TECHNOLOGY 7:929–932 (1989)).

In general, the procedures for expression of C5a in *E. coli* are applicable to C5a analogue gene expression. See, Mandecki, Proc. Natl. Acad. Sci. USA 82:3543–3547 (1985); Mollison et al., Proc. Natl. Acad. Sci. USA 86:292–296 (1989); and Bautsch et al., Immunobiol. 185:41–52 (1992). The choice of suitable regulatory sequences such as promoter (e.g., T7 polymerase, UV5-D, trp or lac), ribosome binding site, as well as suitable plasmid vectors containing transcriptional stop sites, e.g., pKK223-2, are within the level of skill in the art. To optimize expression in *E. coli*, the DNA molecule should be synthesized using *E. coli*-preferred codons as disclosed in Guoy et al., Nucleic Acids Res. 10:7055–7074 (1982), and to allow for several restriction endonuclease sites to facilitate characterization of the synthesized DNA and possibly mutagenesis of the DNA sequence. This approach allows for direct expression of the C5a analogue, by introducing an ATG initiation codon for protein synthesis directly and immediately upstream of the triplet coding for the first amino acid of the polypeptide. Further, *E. coli* strains, e.g., ion, which are deficient in one of several proteases present in wild-type cells offer the advantage of increased yield of protein. Franke et al., Meth. Enzymol. 162:653–658 (1988).

Expression of the C5a analogue genes in hosts such as *E. coli* may also be enhanced by expressing the genes in the form of a fusion protein. Methods; of preparing such fusion proteins using chemically and enzymatically cleavable linkages are known in the art. See, e.g., Smith, in "*Methods in Molecular Biology*," Vol. 3, "New Protein Techniques", pp. 57–70 and 71–88 (1984), and Van Heeke et al., Protein Expression and Purification 4:265–74 (1993). Fusion partners, in general, are those genes (or fragments thereof) which are highly expressed in the host, e.g., *E. coli*. In the case of *E. coli*, suitable fusion partners include endogenous *E. coli* genes and synthetic genes, e.g., containing *E. coli*-preferred codons. In addition, the smaller the size of the fusion partner, the better the yield of the C5a analogue, or derivative thereof. In a preferred embodiment for expression in *E. coli*, the fusion partner is a 159-nucleotide DNA encoding a 53 amino acid fragment of a hybrid of the proteins human interleukin 1 beta and interleukin 1 receptor antagonist (Dinarello, Blood 77:1627–52 (1991)), which DNA contains *E. coli*-preferred codons, and a 24 nucleotide fragment encoding an 8 amino acid linker containing an enterokinase cleavage site and a hydroxylamine sensitive site (Asn-Gly). Those skilled in the art can determine the appropriate size of a fusion partner in accordance with standard techniques (e.g. by determining expression titers of C5a analogue fusion proteins by systematically varying the size (length) of the fusion partner).

In general, the C5a analogue-encoding synthetic genes can be expressed in yeast by following known procedures. See, for example, Romanos et al., Yeast 8:423–488 (1992); Section IV of Goeddel (Ed.), Seth. Enzymol. 185:231–484 (1990); Davidow et al., supra. and U.S. Pat. No. 4,775,622. To optimize expression in yeast, the DNA molecule should be prepared using yeast-preferred codons, particularly to avoid Arg-Arg pairs which are targets for endogenous KEX2 proteases. The use of glutamine, as opposed to methionine, as the N-terminus, facilitates proteolytic cleavage from the signal sequence, e.g., alpha factor signal sequence. It is further preferred to eliminate any potential glycosylation sites such as the asparagine at position 64 of various embodiments of the instant C5a receptor antagonists.

Expression of a C5a analogue-encoding gene of the present invention in mammalian cells can be performed in accordance with known procedures. See Chapter 16, "Expression of Cloned Genes in Mammalian Cells," in Maniatis et al., supra. A representative method of expression in human cells is disclosed in Berg et al., BioTechniques 14(6):972–978 (1993). Suitable human cells include publicly available cell lines such as HeLA S3 (ATCC CCL2.2) and HEK293 (ATCC CRL1573). Expression in CHO cells is disclosed, for example, in Asselbergs et al., Fibrinolysis 7:1–14 (1993). Suitable hamster cell lines include CHO-K1 (ATCC CCL61) and BHK (ATCC CRL6281), BHK-21 (ATCC 6281, CCL10 and CRL8544). Representative monkey cells are CV-1 (ATCC CCL70), COS-7 (ATCC CRL1650), and VERO cells (ATCC CCL81). A suitable mouse cell line is C127 (ATCC 1804). Preferred cell lines are DHFR-minus CHO lines as disclosed in Uriaub et al., Proc. Natl. Acad. Sci. USA 77:4216–4220 (1980). Serum-independent cell lines are more preferred. See Kurano et al., Bio/Technology 16:245–258 (1990). In mammalian hosts, glycosylated or non-glycosylated forms of the C5a analogues can be produced.

The C5a analogues isolated from transformed *E. coli* cells are renatured to assume biological activity wherein the C-terminal cysteine is in reduced form, i,.e., it contains a free thiol group, preferably by using a convenient one-step procedure. Applicants have unexpectedly discovered that treating the denatured C5a analogue with a redox couple in a molar ratio of reducing agent to oxidizing agent from at least about 100:1 to about 500:1 results in a biologically active C5a analogue having a C-terminal cysteine in reduced form. This ratio is from about 10-fold to about 50-fold greater than known ratios (a preferred ratio of reduced sulfhydryl to oxidized sulfhydryl compound of 10:1 is disclosed on col. 17, lines 43–45 of Builder et al., U.S. Pat. No. 4,620,948). In accordance with the procedure, the transformed *E. coli* cells, after culturing under conditions sufficient to cause production of the C5a analogue, are mixed with a denaturing and solubilizing agent, e.g., 6M guanidine HCl, to produce denatured C5a analogue, optionally with further disruption by any known technique such as sonication, French Press or DynoMill. The thus-mixed or thus-disrupted cells containing the denatured C5a analogue are then mixed with a redox couple in a molar ratio by weight of reducing agent/oxidizing agent of from at least about 100:1 to about 500:1 under suitable conditions to produce renatured, biologically active C5a analogue. Suitable redox couples include cysteine/cystine and reduced glutathione/oxidized glutathione. Others skilled in, the art will appreciate that other redox couples can be used. The glutathione redox couple is preferred. Suitable conditions include a pH of from 6.5 to 7.5, preferably 7.4. The mixture is allowed to stand at room temperature for a time sufficient to maximize the yield of protein. The preferred time is from about one-half hour to about 4 hours. Thus, this method eliminates the need to isolate the refractile, inclusion bodies (i.e., the insoluble mass of expressed protein) from the bacterial cells, and then to reduce the thiol group of the C-terminal cysteine.

An embodiment where the C5a analogue or derivative thereof is expressed in the form of a fusion protein, the resultant inclusion body containing fusion protein can be recovered quantitatively after cell lysis using low speed centrifugation (e.g., about 3,000×g), thus providing a relatively highly enriched fraction which then can be appropriately solubilized. This procedure offers the advantage of using a 20-fold decrease in volume per weight of cells recovered from the fermenter.

In the alternative, the C5a analogues may be renatured according to standard refolding and purification schemes such as disclosed in Builder et al., U.S. Pat. No. 4,620,948, for example. Following these procedures, the C-terminal cysteine will be in the form of an adduct, e.g., cys-cys or cys-glutathione. Therefore, the adduct must be further reduced to yield the free thiol group. Applicants have discovered that adducts of the disclosed C5a analogues also function as C5a receptor antagonists which exhibit substantially no agonist activity as defined herein, and thus are included within the scope of the present invention. However, the further reduction would be necessary to prepare the preferred embodiments if these standard renaturation techniques were used.

Following renaturation, the C5a analogues may be purified to the extent desired. Representative purification schemes include ultrafiltration, diafiltration, gel electrophoresis, chromatographic processes such as ion exchange chromatography, size exclusion chromatography, HPLC, reverse phase HPLC, treatment with Sephadex, dialysis, affinity chromatography, etc. Those skilled in the art would appreciate that a combination of purification schemes can be used.

C5a analogues having a C-terminal cysteine residue can be oxidized to form dimers in accordance with standard techniques. To prepare the dimers, the thiol (—SH) groups of the C-terminal cysteines of the respective monomers (analogues) are oxidized to produce a disulfide linkage. Homodimers and heterodimers are embraced by the term "dimer".

The instant C5a analogues and dimers thereof are useful in the treatment and/or prevention of injurious conditions or diseases in which the complement system, and more particularly C5a and analphylatoxin, are involved. They are therapeutically most effective when administered to any mammalian patient, especially humans, who face a high risk of C5a-mediated tissue destruction and death. In general, the conditions or diseases are those such as inflammatory disorders where C5a is generated in the serum proteolytically. Representative conditions responsive to C5a analogue therapy include pneumonitis, adult respiratory distress syndrome (ARDS), idiopathic pulmonary fibrosis, pulmonary inflammation or injury, chronic progressive pulmonary discystic fibrosis, byssinosis, asbestos-induced inflammation, myocardial infarction, post-myocardial infarction inflammation, ischemic heart damage, hepatic cirrhosis, primary biliary cirrhosis inflammation, chronic hepatitis, pancreatitis, hemorrhagic pancreatitis, inflammatory bowel disease, colitis, ischemic brain damage, encephalitis, cranial nerve damage in meningitis, meningitis, uvetis, Purtscher's retinopathy, immune complex-mediated glomerulonephritis, renal cortical necrosis, gout, vasculitis, serum sickness, angio-edema, myasthenia gravis, systemic lupus erythematosis, rheumatoid arthritis, bullous skin disease, hypersensitivity, psoriasis, endotoxin shock, sepsis, severe trauma and burns. They can also be used therapeutically to treat patients suffering from transplant rejection, those receiving immunosuppressive therapy or massive blood transfusion, those exposed to medical devices, and those experiencing pulmonary dysfunction following hemodialysis and leukopheresis.

The analogues and dimers thereof have further therapeutic utility as prophylactics, particularly in conditions caused by reperfusion, e.g., reperfusion following ischemia, and circulatory contact with medical devices, as well as to prevent transplant rejection. In this case, the C5a analogue is administered suitably prior to or substantially simultaneously with the event that is known to cause the inflammation or aggravate an existing inflammatory condition.

The instant C5a analogues and dimers thereof can be administered by any therapeutically effective route for a proteinacecous pharmaceutical, e.g., parenterally, intranasally, rectally or buccally, in dosage unit formulations containing conventional non-toxic pharmaceutically acceptable carriers, adjuvants and vehicles as desired. The term "parenteral" embraces delivery modes such as subcutaneous, intravenous, intramuscular, instrasternal, intra-arterial injection and infusion techniques.

Dosage amounts of the C5a analogues (and diners) of the present invention may be varied to achieve the desired therapeutic response for a particular patient. They will depend, for instance, on the activity of the particular antagonist, the mode of administration, the severity of the condition being treated, as well as the medical condition of the patient. The determination of a therapeutically effective dosage amount for a given condition and patient is within the level of skill in the art. In general, dosage levels of from about 1 ug to 100 mg per kilogram of body weight per day are administered daily to the mammalian host. Preferred dosage levels range from about 0.1 mg/kg to about 20 mg/kg of body weight per day. The C5a analogue is administered to the patient as a single continuous dose over a prolonged period of time. However, the total effective dosage may be divided into multiple doses, e.g., two to four separate doses per day, if desired.

The C5a analogues (and dimers) of the present invention can be formulated into compositions using both known pharmaceutically acceptable ingredients and methods of preparation. See, e.g., Remington et al., *Pharmaceutical Sciences*, 15th Ed., Mack Pub. Easton (1975). Suitable compositions for parenteral administration comprise pharmaceutically acceptable sterile aqueous or nonaqueous solutions, dispersions, suspensions or emulsions, as well as sterile powders for reconstitution into sterile injectable solutions or dispersions immediately prior to use. Representative examples of suitable aqueous and nonaqueous carriers, diluents, solvents or vehicles include water, ethanol, polyols, e.g., glycerol, propylene glycol, polyethylene glycol, and suitable mixtures thereof, vegetable oils, e.g., olive oil, and injectable organic esters such as ethyl oleate. Fluidity may be maintained by various Paeans including the use of coating materials such as lecithin, the maintenance of required particle size (in the case of dispersions) and surfactants.

The compositions may also contain adjuvants such as preservatives, wetting agents, emulsifying agents, dispersing agents, antibacterial and antifungal agents such as paraben, chlorobutanol, phenol and sorbic aid, isotonic agents such as sugars, sodium chloride, or agents which delay absorption such as aluminum monostearate and gelatin. The C5a receptor antagonists may be incorporated into slow or sustained release or targeted delivery systems such as polymer matrices, liposomes and microspheres.

Injectable formulations can be sterilized by numerous means, including filtration through a bacteria-retaining filter, or by incorporating sterilizing agents in the form of sterile solid compositions which can be dissolved or dispersed in sterile water or other sterile injectable medium just prior to use.

Suspensions, in additon to the C5a analogue and any other active ingredient, may contain suspending agents such as ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are usually in the form of suppositories which can be prepared by mixing the polypeptides of the present invention with suitable non-irritating excipients or carriers such as cocoa butter, polyethylene glycol or a suppository wax which is solid at room temperature but liquid at body temperature, and therefore melts in the rectum or vaginal cavity, and releases the C5a receptor antagonist.

Opthalmic formulations, eye ointments, powders and solutions are also included within the scope of the disclosed invention.

Polyclonal and monoclonal antibodies specific to the C5a analogues and dimers of the present invention may be prepared in accordance with standard techniques. Polyclonal antibodies, for example, are raised by injecting a C5a analogue-carrier protein conjugate into an animal, e.g., rabbits, goats, sheep or horses, to raise anti-C5a analogue antibodies. See, e.g., A. Johnstone and R. Thorpe, *Immunochemistry in Practice*, Blackwell Scientific Publications, Oxford (1982). Monoclonal antibodies specific to the C5a analogues of the present invention may be prepared according to the techniques disclosed techniques disclosed in Kohler and Milstein, Nature 256:495–97 (1975). See also Peters, J. H., (eds.) *Monoclonal Antibodies*, Springer Verlag Berlin, Heidelberg, Germany (1992). The polyclonal and monoclonal antibodies specific to the C5a analogues also exhibit substantially no cross-reactivity with human C5a. By the term "substantially no cross-reactivity," it is meant that: the anti-C5a analogue antibodies exhibit extremely low (negligible) cross-reactivity with human C5a such that no interference by endogenously produced C5a with the assay for the instant C5a analogues in biological samples can be detected.

The C5a analogue-specific antibodies of the present invention are particularly useful to detect: and quantify circulating C5a analogue in a subject previously administered with same, as well as in modulating, e.g., neutralizing, the activity of the circulating C5a analogue. Circulating C5a analogue can be detected in accordance with standard immunological techniques which utilize antibodies. In general, a fluid or tissue sample is obtained from the subject and then reacted with an antibody specific to the C5a analogue which was administered to the subject, under conditions suitable to allow for the detectable formation of an immune complex between the analogue and the antibody. The formation of such an immune complex is indicative of the presence of the analogue in the sample. The use of plasma or serum samples in such assays are preferred. However, tissue such as certain blood cells, e.g., PMNL's, can also be used. The presence and/or extent of reaction can be determined in a variety of methods known in the art such as radioimmunoassay, enzyme immunoassay, fluorescent immunoassay, fluorescent microscopy, etc., and the like. Qualitative and quantitative suitable immunological assay methods are disclosed in J. Butler, *Immunochemistry of Solid-Phase Immunoassay,* CRC Press (1991)

Assays to detect circulating C5a analogue are typically employed to monitor levels of the analogue during treatment. In addition, the antibodies of the present invention can be advantageously used in a pharmaceutical composition to modulate or neutralizer the activity of the circulating C5a analog. The amount of antibody used will be a molar equivalent of the amount of analogue administered. The compositions may be administered to a subject parenterally. Intravenous administration is preferred especially in an emergency situation. The antibodies will be formulated in a unit dosage injectable form in association with a pharmaceutically acceptable vehicle such as saline or Ringer's solution.

The invention will be further described by reference to the following detailed examples. These examples are provided for purposes of illustration only, and are not intended to be limiting unless otherwise specified.

EXAMPLE 1

Synthesis Of A Gene Encoding Human C5a

The human C5a gene was synthesized by oligonucleotide coupling. The codon usage of this synthetic gene was designed for optimal expression in *E. coli*. The synthetic strategy is illustrated in FIG. 1. It entailed the condensation of five fragments with the N-terminal residue changed from Thr to Met since the AUG codon gives a much higher frequency of translation initiation than any other codon. Fragment 1 encodes a Shine-Delgarno sequence and the ATG start codon of the synthetic gene. Fragments 2–5 encode the C5a gene.

Oligonucleotide Synthesis:

Oligonucleotides were synthesized on a Gene Assembler (Pharmacia) by the solid phase phosphoramidite method. The fully synthesized oligonucleotides were cleaved from the solid support and deprotected by incubation with concentrated $NH_4OH$ for 16 h at 55° C. The oligonucleotides were then purified by preparative gel electrophoresis. The acrylamide concentration used varied from 10% for oligonucleotides greater than 70 bases to 20% for those less than 40 bases in length. Following electrophoresis, the oligonucleotides were visualized by UV shadowing and. the major high molecular weight fragment was excised from the gel. The gel slice was pulverized in a test tube with a glass rod and the DNA extracted by incubation in 3.0 ml of 0.1 M triethylammoniun bicarbonate (TEAB) buffer at pH 7.5 for 16 h at 37° C.

The gel remnants were removed by centrifugation and the oligonucleotides isolated by chromatography on SepPak C-18 columns (Waters Associates). The columns were pre-equilibrated by washing sequentially with 10 ml acetonitrile, 5 ml 30% acetonitrile in 50 mM TEAB and 10 ml 25 mM TEAB. The oligonucleotides were applied, washed with 10 ml 25 mM TEAB, and eluted from the columns with 5 ml 50% acetonitrile in 35.5 mM TEAB. Fractions were collected and those containing the oligonucleotides, as determined by absorbance at 260 nm, were dried in a SpeedVac (Savant).

Oligonucleotide Annealing and Coupling:

Prior to annealing, each oligonucleotide was phosphorylated at the 5'end. The kinase reaction mixture contained 1 ug of oligonucleotide in a total volume of 40 ul, 77 mM TRIS, at pH 7.5, containing 12 mM $MgCl_2$, 1 mM DTT (dithiothreitol) and 2 mM ATP. The reaction was initiated by the addition of 10 units of T4 polynucleotide kinase and was allowed to 5 proceed for 40 min at 37° C. 10 ul of sterile water were added to each kination reaction and 48 ul of complimentary oligonucleotides were added, mixed and placed in a heating block at 78° C. The heating block was turned off and the mixture was allowed to cool to 30° C. The samples then were placed in a second heating block at 68° C. for 10 min, and again the block was turned off and the mixture allowed to cool to 26° C. Annealed gene fragments were used to assemble the gene in phage M13mp18 (New England Biolabs). The strategy for assembling the C5a encoding gene in M13mp18 required three rounds of ligation reactions.

Figure 2:
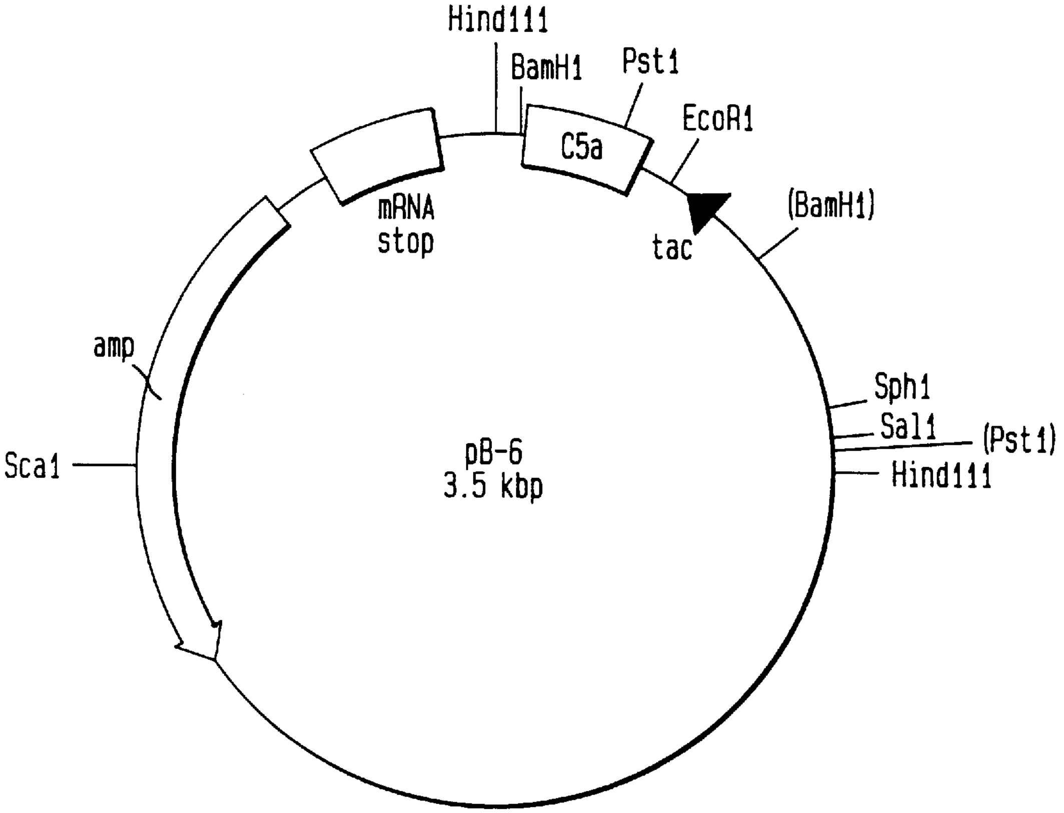

Following each ligation reaction of the appropriate gene fragments into M13mp18, *E. coli* JM101 was transformed with the ligated M13 DNA. Isolation of the M13 phage from the recombinant clones was followed by sequence analysis of the construction. The final C5a gene was cloned into M13mp18 to give M13mp18/C5a(Thr1Met, 1-74). The C5a (1-74) gene was subsequently subcloned into a pB-6 vector, derived from plasmids pTZ19R and pKK223-3 both obtained from Pharmacia) to yield pB-6/C5a(Thr1Met, 1-74). See FIG. 2.

EXAMPLE 2

Site-directed Mutagenesis Of The C5a Gene

Using the oligonucleotide-directed in vitro Mutagenesis System Version 2 (Amersham), the single stranded DNA from the C5a containing vector M13mp18/C5a(1-74) and a mutagenic oligonucleotide, site-directed mutagenesis was performed. The mutation Cys27Ser in C5a was performed using the mutagenic oligonucleotide, ACGGTGCTTCTGT-TAACA (SEQ. ID. NO. 6), following the procedure provided by the manufacturer. Four plaques were analyzed by dideoxy DNA sequencing for the correct Cys27Ser mutation. Double stranded DNA was isolated from one of the correct mutant clones and restricted with PstI and BamHI. A 230 bp fragment containing the mutation was subcloned into the pB-6 vector. The resulting plasmid, pB-6/C5a(1-74, T1M, C27S), was sequenced again via the dideoxy method to confirm the mutation.

EXAMPLE 3

Cassette Mutagenesis Of The C5a Gene

The plasmid pB-6/C5a(1-74, T1M, C27S) or pB-6/C5a (1-74, T1M,) was restricted with EcoRI and HindIII, and subcloned in the vector pWCB, also restricted with the same enzymes, to yield plasmids pWCB112, containing the gene encoding C5a(1-74, T1M, C27S), and pWCB100, containing the gene encoding for C5a(l-74, TLM), respectively. Then, the plasmids were used in cassette mutagenesis to make a series of new genes. Oligonucleotides used in cassette mutagenesis were made with an Applied Biosystems 381A DNA Synthesizer, using solid phase phosphoramidite chemistry according to the instructions of the manufacturer. Ten ul TE, containing about 60 ug of pWC31112, were mixed with 6 μl containing 60 U of PVUII and 3 μl containing 60 U of HindIII (New England Biolabs) and 10 μl of 10 ×High Salt buffer (1M NaCl, 0.5 M Tris/HCl at pH 7.5, 0.1M $MgCl_2$, 10 mM DTT) and 71 μl $ddH_2O$ for a total volume of 100 ul. This solution was incubated at 37° C. for 16 hours. The thus-linearized vector of about 4.5 Kb was purified by preparative electrophoresis using a 1% agorose gel, followed by electroelution of the DNA fragment from the excised agarose gel slice. The recovered DNA fragment was transferred to an Eppendorf tube, 1 ml of absolute ethanol was added and the tube centrifuged for 10 min at 14,000 rpm in an Eppendorf centrifuge. The DNA pellet was dried under vacuum and subsequently dissolved in 45 μl TE buffer (10 mM Tris.HCl at pH 7.4 containing 1 mM EDTA) yielding pWCB112/A. single stranded oligonucleotides a 35 bp- sequence, 5'CTGCGTGCTAACATCTCTCACAAA-GACATGTGCTA3' (SEQ. ID. NO. 7), and a 39 bp-sequence, 5 'AGCTTAGCACATGTCTTTGT-GAGAGATGTTAGCACGCAG3 ' (SEQ. ID. NO. 8), were purified by preparative electrophoresis on a 8% polyacrylamide gel. Following electrophoresis, the oligonucleotides were visualized by UV shadowing and the appropriate fragment excised from the gel. The gel slice was pulverized in a test tube with a glass rod and the DNA extracted by incubation in 3.0 ml of 0.1 M TEAB buffer at pH 7.5 for 16 h at 37° C. The gel remnants were removed by centrifugation and the oligonucleotides isolated by chromatography on SepPak C-18 columns (Waters Associates). The columns were pre-equilibrated by washing sequentially with 10 ml acetonitrile, 5 ml 30% acetonitrile in 50 mM TEAB and 10 ml 25 mM TEAB. The oligonucleotides were applied, washed with 10 ml 25 mhM TEAB, and eluted from the columns with 5 ml 50% acetonitrile in 35.5 mM TEAB.

Fractions were collected and those containing the oligonucleotides, as determined by absorbance at 260 nm, were dried in a SpeedVac (Savant). Annealing of the 35 and 39 bp oligonucleotides to form double stranded DNA for ligation into the restricted vector pWCB112/A was performed by mixing equal amounts of each oligonucleotide with Klenow Buffer, which contains 0.05 M Tris/HCl at pH 7.6 containing 0.01 M $MgCl_2$, heating the sample to 95° C. for 10 min and subsequent cooling to room temperature over a 2 hour period. The double-stranded DNA was ligated into the restricted vector pWCB112 using a 3-fold excess of insert over vector with 1 μl, 2 U, of T4 DNA ligase (BRL). The reaction was run for 17 hours at 4° C.

Using essentially the same technique, a number a molecules were prepared merely by using different oligonucleotides, and either pWCB100 or pWCB112. They are set forth below in Table 2.

analogue No. 8 is described in Example 5c, below. It is designated Analogue No. 22.

The complete nucleotide sequence of the polynucleotide encoding C5a analogue No. 21 is set forth in Table 3 below.

TABLE 2

C5a analogues produced by cassette mutagenesis of the C5a(1-74) or C5a(1-74,C27S) gene

| Analogue No. | oligonucleotide sequences used and encoded C5a analogue |
|---|---|
| 1. | C5a(1-64,T1M,C27S,N64C)<br>CTGCGTGCTTGCTA (SEQ. ID. NO. 9)<br>AGCTTAGCAAGCACGCAG (SEQ. ID. NO. 10) |
| 2. | C5a(1-65,T1M,C27S,I65C)<br>CTGCGTGCTAACTGCTA (SEQ. ID. NO. 11)<br>AGTTAGCAGTTAGCACGCAG (SEQ. ID. NO. 12) |
| 3. | C5a(1-66,T1M,C27S,S66C)<br>CTGCGTGCTAACATCTGCTA (SEQ. ID. NO. 13)<br>AGCTTAGCAGATGTTAGCACGCAG (SEQ. ID. NO. 14) |
| 4. | C5a(1-67,T1M,C27S,H67C)<br>CTGCGTGCTAACATCTCTTGCTA (SEQ. ID. NO. 15)<br>AGCTTAGCAAGAGATGTTAGCACGCAG (SEQ. ID. NO. 16) |
| 5. | C5a(1-68,T1M,C27S,K68C)<br>CTGCGTGCTAACATCTCTCACTGCTA (SEQ. ID. NO. 17)<br>AGCTTAGCAGTGAGAGATGTTAGCACGCAG (SEQ. ID. NO. 18) |
| 6. | C5a(1-69,T1M,C27S,D69C)<br>CTGCGTGCTAACATCTCTCACAAATGCTA (SEQ. ID. NO. 19)<br>AGCTTAGCATTTGTGAGAGATGTTAGCACGCAG (SEQ. ID. NO. 20) |
| 7. | C5a(1-70,T1M,C27S,M70C)<br>CTGCGTGCTAACATCTCTCACAAAGACTGCTA (SEQ. ID. NO. 21)<br>AGCTTAGCAGTCTTTGTGAGAGATGTTAGCACGCAG (SEQ. ID. NO. 22) |
| 8. | C5a(1-71,T1M,C27S,Q71C)<br>CTGCGTGCTAACATCTCTCACAAAGACATGTGCTA (SEQ. ID. NO. 23)<br>AGCTTAGCACATGTCTTTGTGAGAGATGTTAGCACGCAG (SEQ. ID. NO. 24) |
| 9. | C5a(1-72,T1M,C27S,L72C)<br>CTGCGTGCTAACATCTCTCACAAAGACATGCAATGCTA (SEQ. ID. NO. 25)<br>AGCTTAGCATTGCATGTCTTTGTGAGAGATGTTAGCACGCAG (SEQ. ID. NO. 26) |
| 10. | C5a(1-73,T1M,C27S,G73C)<br>CTGCGTGCTAACATCTCTCACAAAGACATGCAACTGTGCTAS (SEQ. ID. NO. 27)<br>AGCTTAGCACAGTTGCATGTCTTTGTGAGAGATGTTAGCACGCAG (SEQ. ID. NO. 28) |
| 11. | C5a(1-74,T1M,C27S,Q71C)<br>CTGCGTGCTAACATCTCTCACAAAGACATGTGCCTGGGTCGTTA (SEQ. ID. NO. 29)<br>AGCTTAACGACCCAGGCACATGTCTTTGTGAGAGATGTTAGCACGCAG (SEQ. ID. NO. 30) |
| 12. | C5a(1-73,T1M,C27S,Q71C)<br>CTGCGTGCTAACATCTCTCACAAAGACATGTGCCTGGGTTA (SEQ. ID. NO. 31)<br>AGCTTAACCCAGGCACATGTCTTTGTGAGAGATGTTAGCACGCAG (SEQ. ID. NO. 32) |
| 13. | C5a(1-72,T1M,C27S,Q71C)<br>CTGCGTGCTAACATCTCTCACAAAGACATGTGCCTGTA (SEQ. ID. NO. 33)<br>AGCTTACAGGCACATGTCTTTGTGAGAGATGTTAGCACGCAG (SEQ. ID. NO. 34) |
| 14. | C5a(1-74,T1M,R74C)<br>CTGCGTGCTAACATCTCTCACAAAGACATGCAACTGGGTTGCTA (SEQ. ID. NO. 35)<br>AGCTTAGCAACCCAGTTGCATGTCTTTGTGAGAGATGTTAGCACGCAG (SEQ. ID. NO. 36) |
| 15. | C5a(1-71,T1M,C27S)<br>CTGCGTGCTAACATCTCTCACAAAGACATGCAATA (SEQ. ID. NO. 37)<br>AGCTTATTGCATGTCTTTGTGAGAGATGTTAGCACGCAG (SEQ. ID. NO. 38) |
| 16. | C5a(1-71,T1M,C27S,Q71D)<br>CTGCGTCCTAACATCTCTCACAAAGACATGGACTA (SEQ. ID. NO. 39)<br>AGCTTAGTCCATGTCTTTGTGAGAGATGTTAGCACGCAG (SEQ. ID. NO. 40) |
| 17. | C5a(1-71,T1M,C27S,Q71S)<br>CTGCGTGCTAACATCTCTCACAAAGACATGTCTTA (SEQ. ID. NO. 41)<br>AGCTTAAGACATGTCTTTGTGAGAGATGTTAGCACGCAG (SEQ. ID. NO. 42) |
| 18. | C5a(1-71,T1M,C27S,Q71H)<br>CTGCGTGCTAACATCTCTCACAAAGACATGCACTA (SEQ. ID. NO. 43)<br>AGCTTAGTGCATGTCTTTGTGAGAGATGTTAGCACGCAG (SEQ. ID. NO. 44) |
| 19. | C5a(1-71,T1M,C27S,Q71R)<br>CTGCGTGCTAACATCTCTCACAAAGACATGCGTTA (SEQ. ID. NO. 45)<br>AGCTTAACGCATGTCTTTGTGAGAGATGTTAGCACGCAG (SEQ. ID. NO. 46) |
| 20. | C5a(1-71,T1M,C27S,Q71L)<br>CTGCGTGCTAACATCTCTCACAAAGACATGCTGTA (SEQ. ID. NO. 47)<br>AGCTTACAGCATGTCTTTGTGAGAGATGTTAGCACGCAG (SEQ. ID. NO. 48) |
| 21. | C5a(1-71,T1M,C27S,H67F,Q71C)<br>CTGCGTGCTAACATCTCTTTCAAAGACATGTGCTA (SEQ. ID. NO. 49)<br>AGCTTAGCACATGTCTTTGAAAGAGATGTTAGCACGCAG (SEQ. ID. NO. 50) |

Analogue Nos. 10–20 are agonists, and are outside the scope of the present invention. They are included for purposes of comparison. The preparation of the dimeric form of

TABLE 3

| |
|---|
| GAA—TTC—CCA—CTC—AAA—ATA—AGG—AGG—AAA—AAA—AA<br>ECOR1 |
| ATG—CTG—CAG—AAG—AAA—ATC—GAA—GAA—ATC—GCT<br>START |
| GCT—AAG—TAC—AAA—CAC—TCT—GTT—GTT—AAA—AAA |
| TGC—TGC—TAC—GAC—GGT—GCT—TCT—GTT—AAC—AAC<br>HPA1 |
| GAC—GAA—ACT—TGC—GAA—CAG—CGT—GCT—GCT—CGT |
| ATC—TCT—CTG—GGC—CCG—CGT—TGC—ATC—AAA—GCA<br>APA1 |
| TTC—ACT—GAA—TGC—TGC—GTT—GTT—GCT—TCT—CAG<br>PVU11 |
| CTG—CGT—GCT—AAC—ATC—TCT—TTC—AAA—GAC—ATG |
| TGC—TAA—GCT—T (SEQ. ID. NO. 51)<br>HIND111 |

However, those skilled in the art will appreciate that many polynucleotides can be prepared encoding the identical C5a analogue, due to the degeneracy of the genetic code. See, e.g., Watson et al., *Recombinant DNA,* 2nd Ed., Freeman, N.Y. (1993).

EXAMPLE 4

Expression Of C5A And C5a Analogues In *E.coli*

To achieve expression, the synthetic genes for the C5a analogues set forth in Table 1 were subcloned in the pWCB vector, the modified expression vector pKK223-3 (Pharmacia) having a BamHI site deleted and a PvuII site changed to a PvuI site, and containing the isopropyl-thio-beta-D-galactoside (IPTG)-inducible tac-promotor, and an ampicillin resistance gene. *E. coil* strain LCIQ, is a derivative of strain LC137 (lon, htpR) disclosed in Goff et al., Proc. Natl. Acad. Sci USA 81:6647–6651 (1984). It contains an F' factor encoding lacIQ, from strain DH5alpha F'IQ (BRL laboratories), and was the host for the expression plasmids. *E. coli* LCIQ containing the appropriate expression plasmid was grown at 30° C. in LB broth until an $OD_{550}$ of 1 was reached. The culture was induced for 3 hours with IPTG at 2.5 mM final concentration. The cells were harvested by centrifugation and stored at −80° C. until use.

EXAMPLE 5a

Refolding And Purification Of C5a And C5a Analogues

Recombinant protein was isolated from the frozen *E. coli* cell paste aliquots from Example 4 after thawing in a buffer containing 6 M guanidinium hydrochloride (5:1 v:w, buffer:cell paste). The cells were then disrupted by sonication, and the product dialyzed overnight against a 50 mM Tris/HCl buffer at pH 8.0 containing either 1 mM cysteine and 1 mM cystine or 1 mM reduced/oxidized glutathione to promote renaturation. The dialysate; was then acidified to pH 3 by the addition of 6 N HCl. The precipitate was removed by centrifugation and the supernatant was purified on a DeltaPak C18,100 Å, 15 micron, reverse phase HPLC column (Waters) using a linear gradient from 25% to 35% acetonitrile in water in the presence of 0.1% TFA over 30 min. The major peak eluting from the column at about 28% acetonitrile was collected and lyophilyzed. This fraction contained the gluthathione adduct of recombinant C5a analogue (adducts of analogues 5, 7, 8, 9, and 21 in Table 1), or the cysteine-adduct of the C5a analogue (the adduct of analogue No. 8, Table 1).

Approximately 0.002 mmoles of the cysteine-adduct of the C5a analogue gene product were dissolved in 50 ml 0.1 M Tris buffer at pH 7.4. 0.02 mmoles of DTT were added. After 4 hours, about 80% of the C-terminal cys-cys linkages was converted to the free cysteine and the product was purified on a C4, 15 micron, 300 Å, reverse phase column (Alltech) using a linear gradient from 25 to 35% acetonitrile in water in the presence of 0.1% TFA for 30 min. Fractions containing the product eluting at about 29% acetonitrile were lyophilized and then stored at 4° C., dessicated under vacuum.

EXAMPLE 5b

Refolding And Purification Of C5a And C5a Analogue

Recombinant protein was isolated from the frozen cell *E. coli* paste aliquots from Example 4 after thawing in a buffer containing 6M guanidinium hydrochloride (5:1 v:w, buffer:cell paste). The cells were then disrupted by sonication and the product was diluted twenty-fold with 100 mM Tris/HCl buffer at pH 7.4 containing 1. mM reduced/0.01 mM oxidized glutathione. After 4 h, the solution was acidified to pH 3 by the addition of 6 N HCl. The resulting precipitate was removed by centrifugation and the supernatant was purified on a DeltaPak C18, 100 Å, 15 micron, reverse phase HPLC column (Waters) using a linear gradient from 25 to 35% acetonitrile in the presence of 0.1% TFA over 30 min. The major peak eluting from the column at about 30% acetonitrile was collected and lyophilized. The thus-isolated C5a analogue had a C-terminal cysteine having a reduced thiol group.

EXAMPLE 5c

Formation Of C5a Analogue Dimers

C5a analogues having in their C-terminal region a free thiol group were converted from the monomeric form (after refolding as described in Example 5b) to a dimeric form.

The recombinant protein was isolated from the frozen *E. coli* paste aliquots from Example 4 after refolding according to Example 5b using a 1 mM reduced/0.01 mM oxidized glutathione mixture in 100 mM Tris/HCl at pH 7.4. After 4 h, the solution was acidified to pH 3 by the addition of 6 N HCl. The resulting precipitate was removed by centrifugation and the supernatant absorbed on a SP-Spherodex\ ion exchange column, equilibrated with 25 mM buffer at pH 7.0. After washing the column with 25 mM Tris at pH 7.0, the C5a analogue was eluted from the column with 25 mM Tris at. pH 7.0, containing 0.75 M NaCl. The partially purified C5a analogue was brought to pH 3.0 with formic acid, and diluted with distilled water to achieve a protein solution having a conductivity of about 45 mS/cm, and absorbed to a SP-High Performance ion exchange column equilibrated in 50 mM formic acid at pH 3.5, containing 0.6 M NaCl. C5a analogue was eluted from the column using a linear gradient from 0.6–1.0 M NaCl in 50 mM formic acid buffer at pH 3.5.

The major peak eluting from the column at about 0.725 M NaCl was collected. The thus-isolated C5a analogue had a C-terminal cysteine having a reduced thiol group. Adjustment of the pH to 7.0 with a 25% aqueous ammonia solution and storage of the solution resulted in a conversion of the molecule to its dimeric form. At pH 7.0 and a protein concentration of about 0.3–0.6 mg/ml and storage at 4°8° C., the conversion was at least 80% completed in 2 days. The dimeric form of the C5a analogue was finally purified on a DeltaPak C18, 100 Å, 15 micron, reverse phase HPLC column (Waters) using a linear gradient from 25% to 40% acetonitrile in the presence of 0.1,) TFA over 30 min. The major peak eluting from the column at about 33% acetonitrile was collected and lyophilized. The thus-isolated molecule was a dimer of the C5a analogue produced by the *E. coli* expression system.

EXAMPLE 6

Receptor Binding Assay

C5a and C5a receptor antagonists were tested for their affinity for the C5a receptor. Binding of [125I] Bolton-Hunter (BH)-labelled C5a, prepared as described in Harris et al., J. Receptor Res. 11:115–128 (1991), to PMNL membranes was measured as described in Rollins et al., J. Biol. Chem. 263:520–526 (1988), with modifications as described in Braunwalder et al., Mol. Immunol. 29(11):1319–1324 (1992). PMNLs were resuspended in Hanks balanced salt solution, without $Ca^{++}$ and $Mg^{++}$ and which contained 10 mM HEPES; at pH 7.3, 2.5 mM $MgCl_2$, 100 units/ml DNAse I, 0.1 mM PMISF, 10 $\mu$g/ml aprotonin and 10 $\mu$g/ml leupeptin. They were then equilibrated at 400 psi for 20 min at 4° C. in a nitrogen cavitation bomb. After evacuation into 3 volumes 0.5 M $KHCO_3$ containing 25 mM EDTA and the protease inhibitors listed above, the gelatinous material was removed with forceps and the mixture was centrifuged at 400xg for 10 min at 4° C. The resulting supernatant was centrifuged at 50,000xg for 60 min at 4° C. The pellets from the aliquots representing $200\times10^6$ cells were stored at −70° C. For binding studies, these membranes were resuspended at an equivalent of $20\times10^6$ cells/ml in 50 mM HEPES at pH 7.3, containing 1 mM $CaCl_2$, 5 mM $MgCl_2$, 0.1 mM PMSF, 0.1% bacitracin and 0.5% BSA. After further 1:75 dilution with the same buffer, 400 ul of this suspension were added to duplicate tubes containing 50 ul of [125I]BH-C5a (specific activity 2200 Ci/mmol, final concentration 4.0 pM), and 50 ul buffer or C5a analogues to be tested at various concentrations for inhibitor properties.

Nonspecific binding was determined in the presence of 10 nM unlabelled C5a. The binding reaction was initiated by the addition of the PMNL membranes and was continued for 120 min at 4° C. Bound and free radioactivity were separated by vacuum filtration through GF/C glass fiber filters (Whatman), pretreated for 90 min with 0.05% PEI (polyethyleneimine) using a Cell Harvester (Brandel, Gaithersburg, Md.). Filters were washed with 3x5 ml of ice-cold 5 mM Tris buffer at pH 7.4 and counted in a multiwell Gamma counter (Genesys). Data were analyzed using the non-linear regression analysis program, RS/1 (Bolt, Beranek and Newman, Boston) and expressed as $IC_{50}$ values. The results are set forth below in Table 4 as $K_i$ values using the Cheng-Presoff equation. See Braunwalder et al., supra

TABLE 4

Receptor binding studies of C5a analogues

| C5a analogue | Receptor Binding $Ki^{(nM)}$ |
|---|---|
| 9 Glutathione | 1.85 |
| 8 Glutathione | 1.7 |
| 7 Glutathione | 7.2 |
| 8 Cys | 2.8 |
| 9 | 0.9 |
| 8 | 0.2 |
| 7 | 0.4 |
| 15* | 3.0 |
| 16* | 8.5 |
| 17* | 7.5 |
| 18* | 0.15 |
| 19* | 0.35 |
| 20* | 0.035 |
| 21 | 0.1 |
| 22 | 0.04 |
| C5a | 0.0035 |

*= agonist; numbers in left column refer to Table 1.

These results demonstrate that the C5a analogues of the present invention competitively displace wild-type C5a with nanomolar $K_i$s.

The C5a analogues of the present invention have an affinity for the C5a receptor measured as a $K_i$ in the competitive displacement assay disclosed in Braunwalder et al., supra. (using the radioligand, [125I]Bolton-Hunter labelled C5a), of less than about $1.0\times10^{-8}$ M, preferably less than about $2.0\times10^{-9}$ M, and more preferably less than about $1.0\times10^{-10}$ M.

EXAMPLE 7

C5A Induced Ca++ Rise

Recombinant human C5a was dissolved in Hanks buffer containing 0.01% Tween-20, and all stock dilutions of C5a were made in this buffer. The acetoxymethyl ester of fura-2 (fura 2AM, Molecular Probes) was dissolved in DMSO. Neutrophils were purified from human peripheral blood by sedimentation in 6% hetastarch (HESPAN, DuPont, Waukegan, Ill.), followed by counter flow elutriation as described in Chapman-Kirkland et al., J. Immunol. Meth. 142:95–104 (1991). Purified cells ($2\times10^6$/ml) were mixed with 0.2 uM fura- 2AM and incubated for 30 min at 37° C. in HEPES buffered Hanks solution without calcium or magnesium. Fifteen minutes before the assay, the cell suspension was transferred to a curvette containing a stir bar and calcium was added to 1 mM. The cell suspension was incubated with stirring at 37° C. Assays were terminated within 5 h of cell purification and a standard control response was obtained periodically to insure that the cell responses were not changing over the time of the experiment. The amount of fluorescence was determined using an SLM 8000 spectrofluorometer (SLM-Aminco Instruments, Urbana, Ill.). Curvettes were placed in the fluorometer and after obtaining a baseline for 10 sec, the C5a receptor antagonists to be tested for antagonistic properties were added and any change in fluoresence excitation ratio of 340 nm/380 nm (emission of 510 nm) was measured. Forty seconds after analogue addition, a challenge dose of C5a was added to a final concentration of 100 pM and the resulting change in excitation ratio was measured.

$IC_{50}$ values were used as a measure of antagonist potency. These values are defined as the concentration of C5a analogue needed to reduce the calcium rise response of the 100 pM C5a challenge dose by 50%. $EC_{50}$ values were used as a measure of agonist potency. $EC_{50}$ is defined as that concentration of C5a analogue that elicited 50% of the maximum calcium rise response produced by the analogue. The results are set forth below in Table 5.

TABLE 5

C5a induced calcium rise studies on C5a analogues

| | Calcium Rise (nm) | |
|---|---|---|
| analogue | $IC_{50}$ (antagonist) | $EC_{50}$ (agonist) |
| 9 glutathione | 1000 | NM(not measurable) |
| 8 glutathione | 2000 | NM |
| 7 glutathione | 2000 | NM |
| 8 cysteine | 105 | NM |
| 9 | 43 | NM |
| 8 | 14 | NM |
| 7 | 54 | NM |
| 15 | NM | 90 |
| 16 | NM | 310 |
| 17 | NM | 120 |
| 18 | NM | 150 |
| 19 | NM | 40 |
| 20 | NM | 75 |
| 21 | 6 | NM |
| 22 | 10 | NM |
| C5a | NM | 0.07 |

Ca5 analogue No. 7 was tested up to a concentration of $1.0\times10^{6}$ M. C5a analogue No. 8 was tested up to a concentration of $3.0\times10^{-6}$ M, analogue No. 9 was tested up to a concentration of $1.5\times10^{6}$ M, and analogue No. 21 was tested up to a concentration of $8.0\times10^{-7}$ M. Agonist activity was not detected in all cases. The results, analyzed collectively with those set forth in Table 2, above, suggest that the analogues of the present invention function as competitive inhibitors of C5a. They demonstrate that the C-terminus of the analogues should be an uncompleted cysteine or a cysteine residue which is complexed through a disulfide linkage with another C5a analogue of the present invention, to achieve the highest potency.

EXAMPLE 8

Rabbit Dermal Model Of Inflammation

All experiments were performed on male New Zealand White rabbits weighing 2.5–3.0 kg. The backs; of the rabbits were shaved and 40–50 skin sites were designated with markers of different colors. Different stimuli (i.e., C5a, C5a analogue, C5a+C5a analogue, vehicle control, etc.) were injected intradermally at 0.1 ml/site using a sterile, disposable, 26 gauge, 0.5 in. needle and 1.0 cc tuberculin syringe. I.D. injections were administered in replicates of six, roughly 45 minutes before euthanization. C5a alone was injected at a dose of 50 ng/site, and the C5a receptor antagonists were co-injected at various concentrations with the same dose of C5a. At 20 minutes prior to euthanization, 18–36 uCi of [125I]-labeled bovine serum albumin in 1.0 ml physiological saline were introduced into the systemic circulation via the marginal auricular vein. At 45 minutes, the rabbit was euthanized with an I.V. overdose of sodium pentobarbital. A 5.0 ml sample of peripheral blood was secured via cardiac puncture, centrifuged at 2000 rpm for 10 minutes, and 1.0 ml of plasma was collected and used as a reference to determine the amount of 125I in the plasma.

After death, the dorsal skin was excised and pinned to a wooden dissecting board. Blood in the major vasculature of the skin was manually expressed toward the periphery. This procedure reduced variation among skin sites and decreased background radioactivity. Inflammatory lesions were then punched out of the skin with the aid of a 15 mm cork borer and mallet and deposited in 12×75 mm polystyrene tubes. Injection sites were then analyzed for their radioactive content using a Gamma Counter (Genesys). The amount of [125I]-bovine serum albumin (BSA) that exuded from the blood vessels and which was localized at the inflammatory sites was found to be directly proportional to the degree of enhancement in vascular permeability. The $ID_{50}$ value of the C5a analogue is the dose of that C5a analogue causing a 50% reduction in the radioactivity produced by 50 ng C5a co-injected at the same site.

C5a analogue No. 8 (in Table 1) was found to possess an $ID_{50}$ of 70 ng/site, and did not cause a pro- inflammatory reaction at the dose of 175 ng/site. This result demonstrates that the analogue is an antagonist: in vivo and does not exhibit agonist properties in vivo.

EXAMPLE 9

C5a-Induced Neutropenia In The Rabbit

All experiments were performed on male New Zealand White rabbits weighing 2.5–3.0 kg. Rabbits were anesthetized with 10 mg/kg xylazine and 50 mg/kg ketamine administered in combination intramuscularly. A 25 gauge butterfly catheter was inserted in the lateral ear vein to use for infusions. Each blood sample (0.2 ml) was collected from the central ear artery into a plastic syringe fitted with a 25 gauge, ⅝ inch needle and charged with 7.5% EDTA as an anticoagulant. Blood was immediately expressed into a microcentrifuge tubes containing 10 microliters of 7.5% EDTA. An initial arterial blood sample (#1) was obtained and immediately thereafter vehicle or the C5a analogue of Example 8 was infused intravenously (bolus injection). Twenty seconds later, a second blood sample (#2) was obtained and twenty seconds thereafter 100 ng of C5a in 0.2 ml were infused intravenously (bolus injection). Twenty seconds later, a third blood (#3) sample was taken. Thirty minutes later, a second round of blood sample (#4)—20 seconds—C5a infusion—20 seconds—blood sample (#5) was performed. Blood samples were evaluated by automated hematologic analysis (Technicon H*1) using software specific for rabbit blood. Reductions in neutrophil counts (number per milliliter) induced by C5a(C5a-induced neutropenia, determined by comparing blood sample #3 to #2 and #5 to #4) were compared between vehicle-treated and C5a analogue-treated animals. The C5a analogue did not alter baseline neutrophil counts from normal; i.e., the C5a analogue did not exhibit agonistic (C5a-like) properties.

C5a-induced neutropenia in the C5a analogue-treated rabbits was significantly (P>0.05) inhibited as compared to vehicle-treated rabbits by 67% and 41% at the 40-second and 30-minute C5a challenge intervals, respectively. These results demonstrate the efficacy of administering the C5a analogues systemically.

EXAMPLE 10

Comparative Receptor Binding And C5a Induced Calcium Rise Of C5a Analogues with the Decapeptide H-Ile-Ser-Phe-Lys-Asp-Met-Gln-Leu-Gly-Arg-OH (SEQ. ID. NO. 52).

Five C5a analogues (Nos. 5, 7, 8, 9 and 10 from Table 2) were prepared and run in C5a receptor binding and C5a receptor calcium rise assays and compared with the synthetic decapeptide disclosed in Table I (No. 14) in Or et al., J. Med. Chem. 35:402–406 (1992). Results of this experiment are shown in Table 6 below.

TABLE 6

| | Receptor Binding | $Ca^{++}$ Rise | |
|---|---|---|---|
| Compound | Ki (nM) | $IC_{50}$ (nM) | $EC_{50}$ (nM) |
| Analogue 5 | 0.06 | 84 | |
| Analogue 7 | 0.35 | 859 | |
| Analogue 8 | 0.04 | 51 | |
| Analogue 9 | 0.15 | 621 | |
| Analogue 10 | 0.03 | | 0.6 |
| C5a(1–74) | 0.0035 | | 0.07 |
| Decapeptide | 5,000 | | 2058 |

These results demonstrate that the C5a analogues of the present invention tested possess a 14,000–125,000 fold greater binding affinity for the receptor than the decapeptide. The above data also show that the C5a analogues of the present invention are C5a receptor antagonists molecules that exhibit substantially no agonist activity, while the decapeptide exhibits significant agonist activity.

EXAMPLE 11

Preparation Of Polyclonal Antibodies Specific To C5a(1-71,T1M,C27S,Q71C)

Antigen preparation 1 mg of C5a(1-71,T1M,C27S,Q71C) was conjugated to 2 mg Keyhole Limpet hemocyanin (KLH) using the Imject\Immunogen EDC conjugation kit from Pierce Chemical Co. (Rockford, Ill., USA), following the manufacturer's directions. Conjugation efficiency was followed by adding 3,500 cpm of $^{125}$I-C5a (New England Nuclear, Boston, Mass.). The final volume of the conjugate was 2.25 ml containing 0.34 mg C5a(1-71,T1M,C27S,Q71C) (0.15 mg/ml) and an estimated 0.9 mg/ml of KLH.

Production of anti-C5a(1-71,T1M,C27S,Q71C) antiserum

C5a(1-71,T1M,C27S,Q71C) conjugate (0.5 ml) was homogenized with 0.5 ml of Freund's Complete Adjuvant (Sigma Chemical Co., St. Louis, Mo). Female New Zealand White rabbits, purchased from Millbrook Farms (Amherst, Mass.), were injected subcutaneously in two sites (0.2 ml homogenate per site) in the scapular areas. After 21 days the procedure was repeated. Further injections were carried out using Freund's Incomplete Adjuvant (Sigma); the third injection was given after a total of 55 days, and a fourth at 126 days. Blood (ca. 30 ml) was taken from the rabbits between 3 and 5 weeks after each injection, allowed to clot and the serum removed.

Peptide immobilization for antibody adsorption

C5a(1-71,T1M,C27S,Q71C) or C5a (1 mg) was conjugated to 2 mg Bovine serum albumin (BSA), using the Imject\Immunogen EDC conjugation kit from Pierce Chemical Co. and $^{125}$I-C5a to follow efficiency, as described above. The final volume of C5a(1-71,T1M,C27S,Q71C)/BSA was 2.25 ml at 0.25 mg/ml C5a(1-71,T1M,C27S,Q71C); for C5a/BSA the final volume was 2.25 ml at 0.32 mg/ml C5a. Both conjugates contained an estimated 0.9 mg/ml BSA.

The two peptide conjugates were dialysed against 0.2M sodium hydrogen carbonate buffered to pH 8.6 with sodium carbonate. For each conjugate, 2 ml of AH(aminohexyl)-Agarose gel (Sigma Chemical Co., St. Louis, Mo.) prewashed in the same buffer was activated by adding gluteraldehyde to a final concentration of 1% v/v and incubating for 15 min at 20° C. The gel was washed thoroughly in buffer to remove gluteraldehyde, then the conjugate solutions were added and incubated at 20° C. for 1 hr. The uncoupled protein was rinsed away from the gel and remaining binding sites were blocked by overnight incubation at 4° C. with 20 ml 0.2M glycylglycine. The gel was packed into a 0.5 cm×10 cm glass column and washed thoroughly with Dulbecco's phosphate-buffered saline pH 7.2 containing 0.1% sodium azide (PBS-A).

Affinity chromatography

Serum from rabbits immunized with C5a(1-71,T1M,C27S,Q71C) was passed through the C5a/BSA column at 2 ml/hr. The absorbed antiserum emerging from the column was collected. The column was washed thoroughly with 0.5M NaCl buffered with 0.05M sodium phosphate to pH 7.2 and containing 0.1% sodium azide. Bound antibody was removed with 3M ammonium thiocyanate. The eluting antibody was detected using an in-line UV monitor reading at 280nm and set at 0.2 OD maximum deflection. On the first two passages of serum the eluting antibody was collected and immediately dialysed against PBS-A, then concentrated by ultrafiltration to around 1 mg/ml. This process was repeated several times for each serum batch. Sera were considered to be absorbed when no more protein was detected eluting from the C5a column.

The absorbed antiserum was then passed through the C5a(1-71,T1M,C27S,Q71C) immuno-absorbent column. Bound antibody was eluted with 3M ammonium thiocyanate and immediately dialysed against PBS-A, then concentrated to ca. 1 mg/ml.

EXAMPLE 12a

Preparation Of Labelled Antibody To Detect bound C5a(1-71.T1M,C27S,Q71C)

The anti-C5a(1-71,T1M,C27S,Q71C) antibody eluted from the C5a column (i.e., antibody which cross-reacts with C5a) was conjugated to alkaline phosphatase: 1.4 it mg of antibody in 1 ml of PBS was added to 5 mg (5,000 units) of alkaline phosphatase (Type VII-T, Sigma Chemical Co.). Gluteraldehyde was added to a final concentration of (0.2% v/v. The mix was incubated at 20° C. for 90 min, then dialysed overnight against PBS-A at 4° C. The buffer was changed to 0.05M Tris buffer, pH 8.0 containing 1 mM magnesium chloride, and dialysed overnight at 4° C.

EXAMPLE 12b

Detection Of Bound C5a(1-71,T1M,C27S,Q71C) Via EILISA

Specifically purified rabbit anti-C5a(1-71,T1M,C27S,Q71C) at 0.57 mg/ml was diluted 1:500 in 0.1M sodium borate/boric acid, pH 8.6. ELISA plates (Maxisorp\, Nunc, Naperville, Ill.) were coated with 100 ul/well of this solution for 4hr at 20° C. The plates were washed three times to remove unbound material. Samples containing C5a(1-71, T1M,C27S,Q71C) or standard preparations of C5a(1-71, T1M,C27S,Q71C), suitably diluted PBS-A+1% BSA (PBS/BSA), were added to the wells in 100 μl, for 4 hr at 20° C. Labelled antibody was added at 1:3000 in 100 μl PBS/BSA and incubated overnight at 4° C. The plates were washed and then enzyme substrate (for alkaline phosphatase, p-nitrophenyl phosphate (Sigma Chemical Co.) at 1 mg/ml in 10% v/v diethylamine pH 9.8) was added. Color development was allowed to proceed at 20° C. in the dark for about 5 hr. The plates were read at 405 nm using a Biomek 1000 (Beckman Instruments, Calif., USA).

Using the same conditions described above, a standard curve of C5a(1-71,T1M,C27S,Q71C) was constructed (data not shown).

EXAMPLE 12c

Specificity Of Affinity Purified Specific Anti-C5a(1-71,T1M,C27S,Q71C)

C5a(1-71,T1M,C27S,Q71C) or C5a was used to coat microtiter plates at 1 μg/well in 100 ul coating buffer for 4 hr at 20° C. The plates were washed and serial dilutions of the antibody eluted from C5a(1-71, T1M, C27S, Q71C) after absorption on C5a were made into the plate wells in 100 μl PBS/BSA. After 4 hr incubation at 20° C., the plates were washed again. Binding of rabbit antibody was detected with goat anti-rabbit/horseradish peroxidase (Pierce Chemical Co.) at 1:1000 in PBS/BSA, 100 μl/well. After incubating with the second antibody for 4 hr at 20° C., the plates were washed and horseradish peroxidase activity demonstrated with 2,2'-azinobis(3-ethylbenzothiazoline)-6 sulfonic acid diammonium salt ABTS substrate (Pierce Chemical Co.). After 30 min development, the color was read at 405 nm.

EXAMPLE 13

Measurement Of C5a(1-71.T1M,C27S,Q71C) In Rabbit Plasma Samples

Blood was sampled into heparin coated tubes from two anesthetized rabbits (#1 and #2) which were then injected intravenously with C5a(1-71,T1M,C27S,Q71C). Blood was collected after a further 30 min interval. A further injection of C5a(1-71,T1M,C27S,Q71C) was then given and blood was again collected after 30 min. This was repeated 4 more times. The samples were centrifuged to remove blood cells, and the plasma was removed and stored at −20° C. until used in the ELISA.

The samples were diluted in PBS/BSA and quantified in the ELISA against the standard curve generated in Example 11. The increase in circulating C5a(1-71,T1M,C27S,Q71C) with time was then determined. No activity could be detected in samples taken from the two rabbits before injection of C5a(1-71,T1M,C27S,Q71C), demonstrating the specificity of the antibody. The results also demonstrate that the antibody exhibits no cross-reactivity with rabbit C5a, and that C5a(1-71,T1M,C27S,Q71C) is not a naturally occurring substance in rabbits.

EXAMPLE 14

Comparison Of C5a(1-71,T1M,C27S,Q71C) In Rabbit Circulation With Standard C5a(1-71,T1M, C27S,Q71C): Use Of The Specific Anti-C5a(1-71, T1M,C27S,Q71C) Antibody As An Antidote For C5a(1-71,T1M,C27S,Q71C)

The plasma sample obtained from the last time point of rabbit #2 (from Example 13) was subjected to serial doubling dilutions and the slope of the curve obtained was compared with the slope of the standard curve. The two slopes were parallel, indicating that C5a(1-71,T1M,C27S, Q71C) which had been circulating in the rabbit still retained its antigenic properties and would be recognized in the ELISA in the same manner as the standard C5a(1-71,T1M, C27S,Q71C). This result also indicates that the analogue would be neutralized by this antibody if removal of the C5a(1-71,T1M,C27S,Q71C) from the circulation should become necessary.

EXAMPLE 15

Preparation Of Monoclonal Anti-C5a(1-71 T1M, C27S,Q71C)

Preparation of monoclonal antibodies was carried out in BALB/c mice using standard procedures developed by K öhler and Milstein, Nature 256:495–497 (1975). The same preparation of the C5a(1-71,T1M,C27S,Q71C) antigen (coupled to KLH) was used to immunize mice. Screening of monoclonal cell lines generated by fusing spleen cells from immunized mice with the hybridoma line P3/NSI/1-Ag4-1 (ATCC TIB 18) was carried out using C5a(1-71,T1M,C27S, Q71C)/BSA and C5a/BSA. In a direct parallel to the procedure carried out with the polyclonal rabbit antisera, those antibodies which only reacted with C5a(1-71,T1M,C27S, Q71C) and not with C5a were used as specific monoclonal anti-C5a(1-71,T1M,C27S,Q71C) antibodies. Those which recognized both were used as detection antibodies, and labelled with alkaline phosphatase.

EXAMPLE 16

Construction Of Gene Fusions Between Human Carbonic Anigdrase II (hCAII) Gene and C5A Receptor Antagonist Gene.

Plasmid pWCB401 contains a DNA sequence coding for the C5a receptor antagonist ((C5a(1-71, Thr1Met, Cys27Ser, Gln71Cys)). This plasmid was prepared using Seq. ID No. 23 in the cassette mutagenesis procedure described in Example 3. This plasmid then was modified by insertion of a double-stranded synthetic oligonucleotide (OL1/OL2; OL1- 5'-AGC TGG GAT CCG ATA TCC-3' (SEQ. ID No. 53), OL2 5'-A GCT GGA TAT CGG ATC CC-3' (SEQ. ID. No. 54)) at the unique HindIII restriction site of pWCB401 using a standard ligation protocol (Maniatis et. al.) to yield plasmid pWCB401BE. This insertion added BamHI and EcoRV restriction sites immediately downstream of the stop codon and eliminated the HindIII site. Then, two more oligonucleotides (OL3/OL4; OL3—5'-A GCT TTC GTT GAC GAC GAC GAT AAA AAC GGT CTG CA-3'(SEQ. ID. No. 55), OL4—5 'G ACC GTT TTT ATC GTC GTC GTC AAC GAA-3'(SEQ. ID. No. 56)) were synthesized, phosphorylated and annealed by standard procedures (Maniatis et al., 1989). This synthesized oligonucleotide links the gene for the C5a receptor antagonist to the hCAII gene and encodes an enterokinase protease-, and an hydroxylamine sensitive cleavage site.

The 222 bp PstI-EcoRV fragment was recovered from pWcB401BE and was ligated in a three-way ligation experiment to the annealed double-stranded oligonucleotides OL3/OL4 and the HindIII and EcoRV digested pBO304ΔRV. pBO304ΔRV is a derivative of pB0304 (Van Heeke et al., Protein Expression and Purification 4: 265–274 (1993)) and was obtained by eliminating the EcoRV restriction site in the tetracycline resistance gene. The product of the three-way ligation was designated plasmid 29A-1, and th e DNA sequence surrounding the cloning junctions including the synthetic oligonucleotides was verified by standard DNA sequencing methods (Maniatis et al.). *E. coli* strains HMS174(DE3)pLysS and BL21(DE3)pLysS both from (NOVAGEN, MADISON, WIS.) were transformed with plasmid 29A-1 and colonies were isolated on Luria Broth agar plates supplemented with tetracycline (Maniatis et al.).

EXAMPLE 17A

Construction Of C5A Fusion Proteins; Determination Of Expression TITERS in *E. coli*

In the course of experiments trying to exchange a fragment of the human interleukin-1B gene (modified with *E. coli*-preferred codons, obtained from British Biotechnology Limited, UK) with a fragment coding for a peptide fragment of human interleukin-1 receptor antagonist (hIL1-RA) by overlap extension PCR, an artifact translational stop codon following the codon for amino acid at position 72 was obtained. A BamHI cleavage site (GGATCC) was later introduced at the stop codon site to facilitate the construction of fusion proteins. The thus-obtained synethic gene is as follows:

| DNA sequence of IL72 flanked by NcoI and GamHI restriction sites | | | | |
|---|---|---|---|---|
| 5'CCATGGCACC | GGTTAGATCT | CTGAACTGCA | CCCTTCGCGA | CTCCCAACAG |
| AAGAGCTTAG | TAATGTCTGG | TCCGTACGAG | CTCAAAGCTC | TGCATCTGCA |
| AGGCCAGGAC | ATGGAACAAC | AGGTTGTATT | CAGCATGAGC | TTCATTGAGC |
| CTCATGCTCT | TGCATTAGGC | CTGAAAGAGA | AGAATCTGTA | CCTCAGCTGC |
| GTACTGAAAG | CTGCGTCTCA | TATGTTGGAT | CC-3' (Seq. ID No. 57) | |

This synthetic gene is flanked by NcoI and BamHI sites and codes for a hybrid protein composed of sequences of human interleukin-1B (hIL-1B) and human interleukin-1 receptor antagonist (hIL1-RA).

This synthetic gene was then cloned as a NcoI-BamHI fragment into plasmid pPLMu resulting in plasmoid pPL-MuIL72. Plasmid pPLMu is plasmid pPLmuSMCori (Buell, G. et al., Nucleic Acids Res. (1985) 13:1023–1038) with the NcoI-HindIII fragment replaced by a multiple cloning site set forth as below:

| Sequence of EcoRI-Hind III fragment in pPLmuSMCori containing the ribosome binding site and multiple cloning site | | | | |
|---|---|---|---|---|
| 5'-GAATTCTTAC | ACTTAGTTAA | ATTGCTAACT | TTATAGATTA | CAAAACTTAG |
| GAGGGTTTTT | ACCATGGTTA | CGAATTCCCG | GGGATCCGTC | GACCTGCAGC |
| CAAGCTT-3' (Seq. ID No. 58) | | | | |

The encoded hybrid protein is composed—counting from its N-terminal methionine—of amino acids 1–47 of hIL-1B, followed by amino acids 52–57 of hIL1-RA followed by amino acids 60–71 of hIL-1B, followed by the amino acid sequence Cys Val Leu Lys Ala Ala Ser (SEQ. ID. No. 59), and a translational stop codon.

*E. coil* strain LC 137 (Goff, S. A. et al., Nat'l Proc. Acad. Sci., USA 81:6647–6651 (1984)) was then transformed with plasmid pPLmuIL72 carrying the compatible plasmid $pcl_{857}$ encoding the thermolabile phage $\lambda CIS_{57}$ repressor. Heat induction resulted in high expression of the hybrid protein as analyzed by SDS-PAGE of heat induced *E. coli* cells (Buell, et al., supra). The hybrid protein encoded by plasmid pPL-MuIL72 was further shortened by PCR using primers C, D and E as 3' primers:

PCR primer

Primer C

5'CTTATAGGATCCAGATTCTTCTCTTTCAGGCCTAATGCAAG (Seq. ID No. 60)

Primer D

5'CTTATAGGATCCAGAGCATGAGGCTCAATGAAG (Seq. ID No. 61)

Primer E

5'CTTATAGGATCCAGATGCAGAGCTTTGAGCTC (Seq. ID No. 62);

and Primer F

5'TATAAGTCCATGGCACCGGTTAG (Seq. ID No. 63), as 5' primer resulting in plasmids pPLMulL33, pPLMulL53 and pPLMulL63, respectively. The sequence GAT (Asp) in all these constructions of the BamHI site is in proper reading frame with the DNA sequence coding for the hybrid protein. Any coding region cloned into this site via BamHI cleavage will be preceeded by the acid labile amino acid sequence Asp-Pro encoded by the sequence GATCCX which is partly contained in the BamHI cleavage sequence. Acid cleavage of the these fusion proteins will liberate the fusion partner through cleavage at the acid labile Asp-Pro site. The constructs in pPLMuIL63 and pPLMuIL53 showed the same amount of hybrid protein expression as the original pPLMuIL72. No expression was observed with pPLMuIL33. Expression levels were determined afters SDS-PAGE and Coomassie® (ICI, Ltd.) Brilliant Blue staining. pPLMuIL33 and PPLMuIL53 were then used to construct fusion proteins with human C5a. A BamHI site coding for an asparagine (GAT) which is in proper reading frame with the following hC5a gene was introduced by primer directed PCR mutagenesis. The BamHI-HindIII-cut C5a fragment was ligated into BamHI-HindIII cut plasmids pPLMuIL33 and pPLMuIL53 resulting in the plasmids pPLMuIL33-C5a and pPLMuIL53-C5a, respectively.

Sequence of IL33-C5a flanked by NcoI and HindIII sites

5'-CCATGGCACC GGTTAGATCT CTGAACTGCA CCCTTCGCGA CTCCCAACAG

AAGAGCTTAG TAATGTCTGG TCCGTACGAG CTCAAAGCTC TGCATCTGGA

TCCCTGCAGA AGAAAATCGA AGAAATCGCT GCTAAGTACA AACACTCTGT

TGTTAAAAAA TGCTGCTACG ACGGTGCTTC TGTTAACAAC GACGAAACTT

GCGAACAGCG TGTCGCTCGT ATCTCTCTGG GCCCGCGTTG CATCAAAGCA

TTCACTGAAT GCTGCGTTGT TGCTTCTCAG CTGCGTGCTA ACATCTCTCA

CAAAGACATG TGCTAA-3' (Seq. ID No. 64)

IL53-C5a sequence flanked by NcoI and HindIII sites

5'-CCATGGCACC GGTTAGATCT CTGAACTGCA CCCTTCGCGA CTCCCAACAG

AAGAGCTTAG TAATGTCTGG TCCGTACGAG CTCAAAGCTC TGCATCTGCA

AGGCCAGGAC ATGGAACAAC AGGTTGTATT CAGCATGAGC TTCATTGAGC

CTCATGCTCT GGATCCCTGC AGAAGAAAAT CGAAGAAATC GCTGCTAAGT

ACAAACACTC TGTTGTTAAA AAATGCTGCT ACGACGGTGC TTCTGTTAAC

AACGACGAAA CTTGCGAACA GCGTGTCGCT CGTATCTCTC TGGGCCCGCG

TTGCATCAAA GCATTCACTG AATGCTGCGT TGTTGCTTCT CAGCTGCGTG

CTAACATCTC TCACAAAGAC ATGTGCTAA-3' (Seq. ID No. 65)

Heat induction of *E. coli* K12 LC 137 carrying pPLMuIL33-C5a and pPLMuIL53-C5a results in high expression of the fusion protein as judged by SDS-PAGE and WESTERN analysis with anti-hC5a polyclonal antibodies.

EXAMPLE 17b

Construction Of A Gene Fusion Between A Fragment Of A Human Interleukin 1 Receptor Antagonist And C5a Analogue The 5' region of plasmid pPLMmIL53-C5a encompassing codons 1–50 was recovered and optimized using PCR for the purpose of expressing a fusion protein with C5aRA. Briefly, the 5' end was adapted to facilitate cloning into the pET-series bacterial expression vectors. The cysteine codon at position 9 was replaced by a serine codon, and the 3' end of the fragment was modified to allow for the fusion with C5aRA and cleavage linker. The following experiments were performed.

The gene encoding the IL1RA fragment was recovered and adapted from plasmid pPLMmIL53-C5a by PCR using standard DNA amplification conditions (Maniatis et al., 1989) and oligonucleotides designated G83 and G84 as primers (G83: 5'-C GCA AGC TTG AGG CTC AAT GAA GCT CAT--3' (Seq. ID No. 66)) (G84: 5'-GGA GAT ATA CAT ATG GCA CCG GTT AGA TCT CTG AAC AGC ACC CTT CGC-3'(SEQ ID No. 67)) . The amplified fragment was digested with restriction endonucleases NdeI and HindIII and recovered from an agarose gel (fragment 1). Plasmid 29A-1 was digested with HindIII and BamHI and the fragment containing the C5aRA gene was recovered (fragment 2). pET9c (*pET System Manual*, 3rd edition, 1993, Novagen) was digested with NdeI and BamHI and used in a three-way ligation experiment with fragments 1 and 2 to construct plasmid 58A-l. In this construct, the gene coding for C5aRa was linked to a modified fragment of the hybrid IL1 gene fragment via a linker sequence that codes for an enterokinase and hydroxylamine cleavage site. *E. coli* strains BL21(DE3)pLysS and HMS174(DE3)pLysS were transformed with p58A-1 and colonies were isolated on Luria Broth agar plates supplemented with kanamycin and chloramphenicol (Maniatis et al., 1989).

EXAMPLE 18

Expression Of C5a Analogue Fusion Proteins In *E. coli*

Expression experiments were performed using standard procedures for the T7/pET expression system described in Studier et al., Methods Enzymol. 185:60–89 (1990), and Van Heeke et al., Protein Expression and Purification 4:265–274 (1993). Briefly, single *E. coli* colonies harboring expression plasmid were grown in Luria Broth supplemented with the appropriate antibiotic for selection until the optical density (measured at 550 min.) reached about 0.6. At this point, IPTG and Zn++ were added to a final concentration of 0.4 mM and 12.5 $\mu$M, respectively. Incubation of cells was continued at either 21°, 30 ° or 37° C. for an additional 2–4 hrs. Cells were harvested by centrifugation and stored at −80° C. until use.

EXAMPLE 19

Hydroxylamine Cleavage Of C5A Analogue Fusion Protein

Recombinant fusion protein was isolated from the frozen *E. coli* paste aliquots from Example 18 after thawing in a 50 mM Tris/HCI buffer, containing 1 mM EDTA at pH 8.0 (5:1 v:w, buffer:cell paste). The cells were then disrupted by sonication, and the crude extract centrifuged for 20 min at 3,000 ×g. The fusion protein-containing pellet was solubilized in a solution containing 0.2 M CAPSO, 2 M $NH_2OH$.HCL, 6 M guanidinium hydrochloride, adjusted to pH 9.3 with LiOH (7:1 v:w, buffer:cell pellet).

The solution was incubated at 37° C. for 7 hours to promote fusion protein cleavage by hydroxylamine to occur in excess of 80%, after which the pH was adjusted to 8.0 with 4 M HCl. The solution, containing in excess of 80% hydroxylamine cleaved fusion protein, was dialyzed against 25 mM Tris.HCL at pH 7.3 overnight. The dialysate was then centrifuged at 30,000 ×g for 20 min and the C5aRA-containing precipitate collected. The precipitate was solubilized in 6 M guanidinium hydrochloride (5:1 v:w, buffer:precipitate), and diluted twenty-fold with 100 mM Tris/HCl buffer at pH 7.4 containing 1 mM reduced/0.01 mM oxidized glutathione as described in Example 5b.

Purification and dimerization were then performed according to the methods as described above.

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appended claims.

We claim:

1. A DNA molecule encoding a polypeptide analogue of human C5a, wherein said analogue is a C5a receptor antagonist that exhibits substantially no agonist activity, and wherein said analogue comprises a C-terminal region which differs from the corresponding C-terminal region of human C5a in that it is truncated by at least two amino acid residues, and contains at least one cysteine residue, provided that the C-terminal amino acid of said region is a cysteine residue, and wherein said analogue comprises an N-terminal region comprising C5a(2-63) or at least one fragment or a conservatively substituted variant thereof.

2. A DNA molecule encoding a polypeptide analogue of human C5a, comprising:

(a) an N-tennlnal region comprising C5a (2-63), and (b) a C-terminal region which differs from the corresponding C-terminal region of C5a in that said C-terminal region is truncated by at least two amino acid residues, and wherein said region contains at least one cysteine residue, provided that the C-terminal amino add of aid region is cysteine, and wherein said polypeptide analogue is a C5a receptor antagonist that exhibits substantially no antagonist activity.

3. The DNA molecule of claim 2 or claim 1, wherein said N-terminal region of said analogue comprises C5a (1-63, Thr1Met).

4. The DNA molecule of claim 2 or claim 1, which encodes C5a (1-71, Thr1Met, Gln71Cys).

5. The DNA molecule of claim 2 or claim 1, which encodes C5a (1-71, Thr1Met, His67Phe, Gln71Cys).

6. the DNA molecule of claim 2 or claim 1, wherein said N-terminal region of said analogue comprised C5a (1-63, Thr1Gly).

7. A DNA molecule encoding a polypeptide analogue of human C5a, comprising:

(a) an N terminal region comprising C5a (2-63, Cys27Ser), and (b) a C-terminal region which differs from the corresponding C-terminal region of C5a in that said C-terminal region is truncated by at least two amino acid residues, and said region contains at least one cysteine residue, provided that the C-terminal amino acid of said region is cysteine, and wherein said polypeptide analogue is a C5a receptor antagonist that exhibits substantially no agonist activity.

8. The DNA molecule of claim 7 or claim 1, which encodes C5(1-71, Thr1Met, Cys27Ser, Gln71Cys).

9. The DNA molecule of claim 7 or claim 1, which encodes C5a (1-71, Thr1Gly, Cys27Ser, His67Phe, Gln71Cys).

10. The DNA molecule of claim 7 or claim 1, which encodes C5a (1-71, Thr1Gly, Cys27Ser, His 67Phe, Gln71Cys).

11. The DNA molecule of any one of claims 1, 2 or 7, wherein said analogue is from 64 to 72 amino acids in length.

12. The DNA molecule of any one of claims 1, 2, or 7, wherein said analogue is from 64 to 72 amino acids in length.

13. The DNA molecule of any one of claims 1, 2, or 3, wherein said analogue is from 68 to 72 amino acids in length.

14. The DNA molecule of any one of claims 1, 2, or 3, wherein said analogue is from 70 to 72 amino acids in length.

15. The DNA molecule of any one of claims 1, 2, or 3, wherein said analogue is 71 amino acids in length.

16. A recombinant DNA molecule, comprising a promoter capable of functioning in a given host operably linked to the DNA molecule of any one of claims 1, 2, or 3.

17. A recombinant plasmid compatible with a given host, comprising the recombinant DNA molecule of claim 16.

18. A recombinant vector compatible with a given host, comprising the recombinant DNA molecule of claim 16.

19. A recombinant host cell stably transformed with the recombinant DNA molecule of claim 16.

20. The recombinant host of claim 19, selected from the group consisting of bacterial, yeast, fungal, insect, mammalian and plant cells.

21. The recombinant host cell of claim 19, which is *E. coli.*

22. The recombinant host cell of claim 19, wherein said DNA molecule encodes C5a (1-71, Thr1Met, Cys27Ser, Gln71Cys).

23. The recombinant host cell of claim 19, wherein said DNA molecule encodes C5a (1-71, Thr1Gly, Cys27Ser, Gln71Cys).

24. A method of preparing a biologically active human C5a analogue, wherein said analogue is a C5a receptor antagonist that exhibits substantially no agonist activity, and wherein said analogue comprises a C-terminal region which differs from the corresponding C-terminal region of human C5a in that it is truncated by at least two amino acid residues, and contains at least one cysteine residue, provided that the C-terminal amino acid of said region is a cysteine residue, and wherein said analogue comprises an N-terminal region comprising C5a(2-63) or least one fragment or a conservatively substituted variant thereof, comprising the steps of:

culturing *E. coli* cells stably transformed with a DNA molecule encoding the C5a analogue under conditions suitable to cause expression of the DNA molecule;

contacting the thus-cultured cells with a denaturing and solubilizing agent to produce the c5a analogue in denatured form; and mixing the thus denatured C5a analogue with a solution containing a reducing agent and an oxidizing agent in a molar ratio of the reducing agent to the oxidizing agent by, weight of at least about 100:1 under suitable conditions to produce the C5a analogue in biologically active form.

25. The method of claim 24, wherein said mixing is conducted at a pH of from about 6.5 to about 7.5.

26. The method of claim 24, wherein said mixing is conducted from about ½ hour to about 4 hours.

27. The method of claim 24, wherein said the redox couple is reduced glutathione/oxidized glutathione.

28. The method of claim 24, wherein said DNA molecule encodes the C5a analogue in the form of a fusion protein.

29. The method of claim 28, further comprising the step of cleaving the thus-expressed fusion protein prior to said step of mixing.

30. The method of claim 24, wherein DNA molecule encodes a polypeptide analogue of human C5a, (a) wherein said N-terminal region of said analogue comprised C5a (2-63).

31. The method of claim 30, wherein said N-terminal region of said analogue comprises C5a (1-63, Thr1Met).

32. The method of claim 30, wherein said DNA molecule encodes C5a (1-71, Thr1Met, Gln71Cys).

33. The method of claim 30, wherein said DNA molecule encodes C5a (1-71, Thr1Met, His 67Phe, Gln71Cys).

34. The method of claim 30, wherein said N-terminal region of said analogue comprises C5a (1-63, Thr1Gyn).

35. The method of claim 24, wherein said DNA molecule encodes a polypeptide analogue of human C5a, (a) wherein said N-terminal region of said analogue comprises C5a (2-63) (Cys27Ser).

36. The method of claim 35, wherein said DNA molecule encodes C5a (1-71, Thr1Met, Cys27Ser, Gln71Cys).

37. The method of claim 35, wherein said DNA molecule encodes C5a (1-71, Thr1Met, Cys27Ser, His67Phe, Gln71Cys).

38. The method of claim 24, wherein said analogue has a glycine residue as the N-terminus.

39. The method of claim 24, wherein said DNA molecule encodes C5a (1-71, Thr1Gly, Cys27Ser, Gln71Cys).

40. The method of claim 24, wherein said DNA molecule encodes C5a (1-71, Thr1Gly, Cys27Ser, His67Phe, Gln71Cys).

41. A method of preparing a biologically active human C5a analogue, wherein said analogue is a C5a receptor antagonist that exhibits substantially no agonist activity, and wherein said analogue comprises a C-terminal region which differs from the corresponding C-terminal region of human C5a in that it is truncated by at least two amino acid residues, and contains at least one cysteine residue, provided that the C-terminal amino acid of said region is a cysteine residue, and wherein said analogue comprises an N-terminal region comprising C5a(2-63) or at least one fragment or a conservatively substituted variant thereof, comprising the steps of:

culturing host cells stably transformed with a recombinant DNA molecule encoding the C5a analogue in the form of a fusion protein wherein said culturing is conducted under conditions suitable to cause expression of said fusion protein;

isolating the fusion protein from the thus-cultured host cells; and cleaving the thus-isolated fusion protein so that the C5a analogue can be obtained.

42. The method of claim 41, wherein said host cells are *E. coli* cells.

43. The method of claim 41, wherein said analogue has a glycine residue as the N-terminus.

44. The method of claim 41, wherein said recombinant DNA molecule encodes C5a (1-71, Thr1Gly, Cys27Ser, Gln71Cys).

45. The method of claim 41, wherein said recombinant DNA molecule encodes C5a (1-71, Thr1Gly, Cys27Ser, His67Phe, Gln71Cys).

* * * * *

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Tyr Asp Gly Ala
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Asp Gly Ala Tyr
1

( 2 ) INFORMATION FOR SEQ ID NO:3:

( i ) SEQUENCE CHARACTERISTICS:
( A ) LENGTH: 74 amino acids
( B ) TYPE: amino acid
( D ) TOPOLOGY: linear ( i i ) MOLECULE TYPE: protein ( x i ) SEQUENCE DESCRIPTION: SEQ ID NO:3:

Thr Leu Gln Lys Lys Ile Glu Glu Ile Ala Ala Lys Tyr Lys His Ser
1 5 10 15

Val Val Lys Lys Cys Cys Tyr Asp Gly Ala Cys Val Asn Asn Asp Glu
20 25 30

Thr Cys Glu Gln Arg Ala Ala Arg Ile Ser Leu Gly Pro Arg Cys Ile
35 40 45

Lys Ala Phe Thr Glu Cys Cys Val Val Ala Ser Gln Leu Arg Ala Asn
50 55 60

Ile Ser His Lys Asp Met Gln Leu Gly Arg
65 70

( 2 ) INFORMATION FOR SEQ ID NO:4:

( i ) SEQUENCE CHARACTERISTICS:
( A ) LENGTH: 239 base pairs
( B ) TYPE: nucleic acid
( C ) STRANDEDNESS: double
( D ) TOPOLOGY: linear ( x i ) SEQUENCE DESCRIPTION: SEQ ID NO:4:

AATTCTATGA CTCTGCAAAA GAAGATCGAA GAAATCGCTG CTAAGTACAA GCACTCCGTC 60

GTTAAGAAGT GTTGTTACGA TGGTGCATGC GTCAACAACG ACGAAACCTG TGAACAACGA 120

GCTGCTCGTA TTTCTCTGGG CCCTCGCTGT ATCAAGGCTT TCACTGAATG TTGTGTTGTC 180

GCTTCCCAAC TGCGCGCTAA CATTTCTCAC AAGGACATGC AACTCGGCCG CTAAAAGCT 239

( 2 ) INFORMATION FOR SEQ ID NO:5:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:5:

Asn Ile Ser His Lys Asp Met Gln Leu Gly Arg
1 5 10

( 2 ) INFORMATION FOR SEQ ID NO:6:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:6:

ACGGTGCTTC TGTTAACA 18

( 2 ) INFORMATION FOR SEQ ID NO:7:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:7:

CTGCGTGCTA ACATCTCTCA CAAAGACATG TGCTA 35

( 2 ) INFORMATION FOR SEQ ID NO:8:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:8:

AGCTTAGCAC ATGTCTTTGT GAGAGATGTT AGCACGCAG 39

( 2 ) INFORMATION FOR SEQ ID NO:9:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:9:

CTGCGTGCTT GCTA 14

( 2 ) INFORMATION FOR SEQ ID NO:10:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:10:

AGCTTAGCAA GCACGCAG 18

( 2 ) INFORMATION FOR SEQ ID NO:11:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:11:

CTGCGTGCTA ACTGCTA 17

( 2 ) INFORMATION FOR SEQ ID NO:12:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:12:

AGCTTAGCAG TTAGCACGCA G 21

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:13:

CTGCGTGCTA ACATCTGCTA 20

( 2 ) INFORMATION FOR SEQ ID NO:14:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:14:

AGCTTAGCAG ATGTTAGCAC GCAG 24

( 2 ) INFORMATION FOR SEQ ID NO:15:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:15:

CTGCGTGCTA ACATCTCTTG CTA 23

( 2 ) INFORMATION FOR SEQ ID NO:16:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:16:

AGCTTAGCAA GAGATGTTAG CACGCAG 27

( 2 ) INFORMATION FOR SEQ ID NO:17:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:17:

CTGCGTGCTA ACATCTCTCA CTGCTA 26

( 2 ) INFORMATION FOR SEQ ID NO:18:

( i ) SEQUENCE CHARACTERISTICS:
( A ) LENGTH: 30 base pairs ( B ) TYPE: nucleic acid
( C ) STRANDEDNESS: single
( D ) TOPOLOGY: linear ( x i ) SEQUENCE DESCRIPTION: SEQ ID NO:18:

AGCTTAGCAG TGAGAGATGT TAGCACGCAG 30

( 2 ) INFORMATION FOR SEQ ID NO:19:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:19:

CTGCGTGCTA ACATCTCTCA CAAATGCTA 29

( 2 ) INFORMATION FOR SEQ ID NO:20:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:20:

AGCTTACGAT TTGTGAGAGA TGTTAGCACG CAG 33

( 2 ) INFORMATION FOR SEQ ID NO:21:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:21:

CTGCGTGCTA ACATCTCTCA CAAAGACTGC TA 32

( 2 ) INFORMATION FOR SEQ ID NO:22:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:22:

AGCTTAGCAG TCTTTGTGAG AGATGTTAGC ACGCAG 36

( 2 ) INFORMATION FOR SEQ ID NO:23:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:23:

CTGCGTGCTA ACATCTCTCA CAAAGACATG TGCTA 35

( 2 ) INFORMATION FOR SEQ ID NO:24:

( i ) SEQUENCE CHARACTERISTICS:
( A ) LENGTH: 39 base pairs
( B ) TYPE: nucleic acid
( C ) STRANDEDNESS: single -continued ( D ) TOPOLOGY: linear ( x i ) SEQUENCE DESCRIPTION: SEQ ID NO:24:

AGCTTAGCAC ATGTCTTTGT GAGAGATGTT AGCACGCAG 39

( 2 ) INFORMATION FOR SEQ ID NO:25:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:25:

CTGCGTGCTA ACATCTCTCA CAAAGACATG CAATGCTA 38

( 2 ) INFORMATION FOR SEQ ID NO:26:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( x i ) SEQUENCE DESCRIPTION: SEQ ID NO:26:

AGCTTAGCAT TGCATGTCTT TGTGAGAGAT GTTAGCACGC AG 42

( 2 ) INFORMATION FOR SEQ ID NO:27:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:27:

CTGCGTGCTA ACATCTCTCA CAAAGACATG CAACTGTGCT A 41

( 2 ) INFORMATION FOR SEQ ID NO:28:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:28:

AGCTTAGCAC AGTTGCATGT CTTTGTGAGA GATGTTAGCA CGCAG 45

( 2 ) INFORMATION FOR SEQ ID NO:29:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( x i ) SEQUENCE DESCRIPTION: SEQ ID NO:29:

CTGCGTGCTA ACATCTCTCA CAAAGACATG TGCCTGGGTC GTTA 44

( 2 ) INFORMATION FOR SEQ ID NO:30:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO:30:

AGCTTAACGA CCCAGGCACA TGTCTTTGTG AGAGATGTTA GCACGCAG 48

( 2 ) INFORMATION FOR SEQ ID NO:31:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:31:

CTGCGTGCTA ACATCTCTCA CAAAGACATG TGCCTGGGTT A 41

( 2 ) INFORMATION FOR SEQ ID NO:32:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:32:

AGCTTAACCC AGGCACATGT CTTTGTGAGA GATGTTAGCA CGCAG 45

( 2 ) INFORMATION FOR SEQ ID NO:33:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:33:

CTGCGTGCTA ACATCTCTCA CAAAGACATG TGCCTGTA 38

( 2 ) INFORMATION FOR SEQ ID NO:34:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( x i ) SEQUENCE DESCRIPTION: SEQ ID NO:34:

AGCTTACAGG CACATGTCTT TGTGAGAGAT GTTAGCACGC AG 42

( 2 ) INFORMATION FOR SEQ ID NO:35:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( x i ) SEQUENCE DESCRIPTION: SEQ ID NO:35:

CTGCGTGCTA ACATCTCTCA CAAAGACATG CAACTGGGTT GCTA 44

( 2 ) INFORMATION FOR SEQ ID NO:36:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO:36:

-continued

AGCTTAGCAA CCCAGTTGCA TGTCTTTGTG AGAGATGTTA GCACGCAG 48

( 2 ) INFORMATION FOR SEQ ID NO:37:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:37:

CTGCGTGCTA ACATCTCTCA CAAAGACATG CAATA 35

( 2 ) INFORMATION FOR SEQ ID NO:38:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:38:

AGCTTATTGC ATGTCTTTGT GAGAGATGTT AGCACGCAG 39

( 2 ) INFORMATION FOR SEQ ID NO:39:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:39:

CTGCGTCCTA ACATCTCTCA CAAAGACATG GACTA 35

( 2 ) INFORMATION FOR SEQ ID NO:40:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:40:

AGCTTAGTCC ATGTCTTTGT GAGAGATGTT AGCACGCAG 39

( 2 ) INFORMATION FOR SEQ ID NO:41:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:41:

CTGCGTGCTA ACATCTCTCA CAAAGACATG TCTTA 35

( 2 ) INFORMATION FOR SEQ ID NO:42:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:42:

AGCTTAAGAC ATGTCTTTGT GAGAGATGTT AGCACGCAG 39

-continued ( 2 ) INFORMATION FOR SEQ ID NO:43:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:43:

CTGCGTGCTA ACATCTCTCA CAAAGACATG CACTA 35

( 2 ) INFORMATION FOR SEQ ID NO:44:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:44:

AGCTTAGTGC ATGTCTTTGT GAGAGATGTT AGCACGCAG 39

( 2 ) INFORMATION FOR SEQ ID NO:45:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:45:

CTGCGTGCTA ACATCTCTCA CAAAGACATG CGTTA 35

( 2 ) INFORMATION FOR SEQ ID NO:46:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:46:

AGCTTAACGC ATGTCTTTGT GAGAGATGTT AGCACGCAG 39

( 2 ) INFORMATION FOR SEQ ID NO:47:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:47:

CTGCGTGCTA ACATCTCTCA CAAAGACATG CTGTA 35

( 2 ) INFORMATION FOR SEQ ID NO:48:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:48:

AGCTTACAGC ATGTCTTTGT GAGAGATGTT AGCACGCAG 39

( 2 ) INFORMATION FOR SEQ ID NO:49:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:49:

CTGCGTGCTA ACATCTCTTT CAAAGACATG TGCTA 35

( 2 ) INFORMATION FOR SEQ ID NO:50:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:50:

AGCTTAGCAC ATGTCTTTGA AAGAGATGTT AGCACGCAG 39

( 2 ) INFORMATION FOR SEQ ID NO:51:

( i ) SEQUENCE CHARACTERISTICS:
( A ) LENGTH: 252 base pairs
( B ) TYPE: nucleic acid
( C ) STRANDEDNESS: single
( D ) TOPOLOGY: linear ( x i ) SEQUENCE DESCRIPTION: SEQ ID NO:51:

GAATTCCCAC TCAAAATAAG GAGGAAAAAA AAATGCTGCA GAAGAAAATC GAAGAAATCG 60

CTGCTAAGTA CAAACACTCT GTTGTTAAAA AATGCTGCTA CGACGGTGCT TCTGTTAACA 120

ACGACGAAAC TTGCGAACAG CGTGCTGCTC GTATCTCTCT GGGCCCGCGT TGCATCAAAG 180

CATTCACTGA ATGCTGCGTT GTTGCTTCTC AGCTGCGTGC TAACATCTCT TTCAAAGACA 240

TGTGCTAAGC TT 252

( 2 ) INFORMATION FOR SEQ ID NO:52:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:52:

Ile Ser Phe Lys Asp Met Gln Leu Gly Arg
1 5 10

( 2 ) INFORMATION FOR SEQ ID NO:53:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:53:

AGCTGGGATC CGATATCC 18

( 2 ) INFORMATION FOR SEQ ID NO:54:

( i ) SEQUENCE CHARACTERISTICS:
( A ) LENGTH: 18 base pairs
( B ) TYPE: nucleic acid
( C ) STRANDEDNESS: single ( D ) TOPOLOGY: linear ( x i ) SEQUENCE DESCRIPTION: SEQ ID NO:54:

AGCTGGATAT CGGATCCC 18

( 2 ) INFORMATION FOR SEQ ID NO:55:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:55:

AGCTTTCGTT GACGACGACG ATAAAAACGG TCTGCA 36

( 2 ) INFORMATION FOR SEQ ID NO:56:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:56:

GACCGTTTTT ATCGTCGTCG TCAACGAA 28

( 2 ) INFORMATION FOR SEQ ID NO:57:

( i ) SEQUENCE CHARACTERISTICS:
( A ) LENGTH: 232 base pairs
( B ) TYPE: nucleic acid
( C ) STRANDEDNESS: single
( D ) TOPOLOGY: linear ( x i ) SEQUENCE DESCRIPTION: SEQ ID NO:57:

CCATGGCACC GGTTAGATCT CTGAACTGCA CCCTTCGCGA CTCCCAACAG AAGAGCTTAG 60

TAATGTCTGG TCCGTACGAG CTCAAAGCTC TGCATCTGCA AGGCCAGGAC ATGGAACAAC 120

AGGTTGTATT CAGCATGAGC TTCATTGAGC CTCATGCTCT TGCATTAGGC CTGAAAGAGA 180

AGAATCTGTA CCTCAGCTGC GTACTGAAAG CTGCGTCTCA TATGTTGGAT CC 232

( 2 ) INFORMATION FOR SEQ ID NO:58:

( i ) SEQUENCE CHARACTERISTICS:
( A ) LENGTH: 107 base pairs
( B ) TYPE: nucleic acid
( C ) STRANDEDNESS: single
( D ) TOPOLOGY: linear ( x i ) SEQUENCE DESCRIPTION: SEQ ID NO:58:

GAATTCTTAC ACTTAGTTAA ATTGCTAACT TTATAGATTA CAAAACTTAG GAGGGTTTTT 60

ACCATGGTTA CGAATTCCCG GGGATCCGTC GACCTGCAGC CAAGCTT 107

( 2 ) INFORMATION FOR SEQ ID NO:59:

( i ) SEQUENCE CHARACTERISTICS:
( A ) LENGTH: 7 amino acids
( B ) TYPE: amino acid
( D ) TOPOLOGY: linear ( x i ) SEQUENCE DESCRIPTION: SEQ ID NO:59:

Cys Val Leu Lys Ala Ala Ser
1 5

( 2 ) INFORMATION FOR SEQ ID NO:60:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:60:

CTTATAGGAT CCAGATTCTT CTCTTTCAGG CCTAATGCAA G 41

( 2 ) INFORMATION FOR SEQ ID NO:61:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:61:

CTTATAGGAT CCAGAGCATG AGGCTCAATG AAG 33

( 2 ) INFORMATION FOR SEQ ID NO:62:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:62:

CTTATAGGAT CCAGATGCAG AGCTTTGAGC TC 32

( 2 ) INFORMATION FOR SEQ ID NO:63:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:63:

TATAAGTCCA TGGCACCGGT TAG 23

( 2 ) INFORMATION FOR SEQ ID NO:64:

( i ) SEQUENCE CHARACTERISTICS:
( A ) LENGTH: 316 base pairs
( B ) TYPE: nucleic acid
( C ) STRANDEDNESS: single
( D ) TOPOLOGY: linear ( x i ) SEQUENCE DESCRIPTION: SEQ ID NO:64:

CCATGGCACC GGTTAGATCT CTGAACTGCA CCCTTCGCGA CTCCCAACAG AAGAGCTTAG 60

TAATGTCTGG TCCGTACGAG CTCAAAGCTC TGCATCTGGA TCCCTGCAGA AGAAAATCGA 120

AGAAATCGCT GCTAAGTACA AACACTCTGT TGTTAAAAAA TGCTGCTACG ACGGTGCTTC 180

TGTTAACAAC GACGAAACTT GCGAACAGCG TGTCGCTCGT ATCTCTCTGG GCCCGCGTTG 240

CATCAAAGCA TTCACTGAAT GCTGCGTTGT TGCTTCTCAG CTGCGTGCTA ACATCTCTCA 300

CAAAGACATG TGCTAA 316

( 2 ) INFORMATION FOR SEQ ID NO:65:

( i ) SEQUENCE CHARACTERISTICS:
( A ) LENGTH: 379 base pairs
( B ) TYPE: nucleic acid -continued ( C ) STRANDEDNESS: single
( D ) TOPOLOGY: linear ( x i ) SEQUENCE DESCRIPTION: SEQ ID NO:65:

```
CCATGGCACC GGTTAGATCT CTGAACTGCA CCCTTCGCGA CTCCCAACAG AAGAGCTTAG    60
TAATGTCTGG TCCGTACGAG CTCAAAGCTC TGCATCTGCA AGGCCAGGAC ATGGAACAAC   120
AGGTTGTATT CAGCATGAGC TTCATTGAGC CTCATGCTCT GGATCCCTGC AGAAGAAAAT   180
CGAAGAAATC GCTGCTAAGT ACAAACACTC TGTTGTTAAA AAATGCTGCT ACGACGGTGC   240
TTCTGTTAAC AACGACGAAA CTTGCGAACA GCGTGTCGCT CGTATCTCTC TGGGCCCGCG   300
TTGCATCAAA GCATTCACTG AATGCTGCGT TGTTGCTTCT CAGCTGCGTG CTAACATCTC   360
TCACAAAGAC ATGTGCTAA                                                379
```

( 2 ) INFORMATION FOR SEQ ID NO:66:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:66:

```
CGCAAGCTTG AGGCTCAATG AAGCTCAT                                       28
```

( 2 ) INFORMATION FOR SEQ ID NO:67:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO:67:

```
GGAGATATAC ATATGGCACC GGTTAGATCT CTGAACAGCA CCCTTCGC                 48
```